(12) United States Patent
Shigeta et al.

(10) Patent No.: US 10,973,242 B2
(45) Date of Patent: Apr. 13, 2021

(54) PROTEIN-CONTAINING COMPOSITIONS

(71) Applicant: WILD EARTH, INC., Berkeley, CA (US)

(72) Inventors: Ron Shigeta, Berkeley, CA (US); Ryan Bethencourt, Oakland, CA (US); Abril Estrada, Oakland, CA (US)

(73) Assignee: Wild Earth, Inc., Berkeley, CA (US)

( * ) Notice: Subject to any disclaimer, the term of this patent is extended or adjusted under 35 U.S.C. 154(b) by 0 days.

(21) Appl. No.: 16/406,801

(22) Filed: May 8, 2019

(65) Prior Publication Data

US 2019/0350225 A1 Nov. 21, 2019

Related U.S. Application Data

(63) Continuation of application No. 16/133,619, filed on Sep. 17, 2018, now abandoned, which is a (Continued)

(51) Int. Cl.
*A23K 20/147* (2016.01)
*A23K 10/16* (2016.01)
(Continued)

(52) U.S. Cl.
CPC ............. *A23K 10/16* (2016.05); *A23J 1/008* (2013.01); *A23K 10/18* (2016.05); *A23K 20/147* (2016.05);
(Continued)

(58) Field of Classification Search
CPC ...... A23K 10/16; A23K 20/147; A23K 40/00; C07K 14/395; C07K 14/38
(Continued)

(56) References Cited

U.S. PATENT DOCUMENTS 3,438,780 A 4/1969 Singer et al.
3,829,363 A 8/1974 Rogers et al.
(Continued)

FOREIGN PATENT DOCUMENTS

CA 2205712 A1 6/1998
CN 101755871 A 6/2010
(Continued)

OTHER PUBLICATIONS

Abdeen, M. E. et al. Effect of adding fugi biomass on the physicochemical and sensory properties of biscuits. Food Technology Department. Giza, Egypt. 2015 (Year: 2015).*
(Continued)

*Primary Examiner* — Hamid R Badr
(74) *Attorney, Agent, or Firm* — John R. Storella

(57) ABSTRACT

The present disclosure provides a composition comprising (i) at least about 20% protein by dry weight, wherein said protein is not animal-derived protein, (ii) at least 20% by dry weight intact yeast cells, (iii) 20% to 70% plant-derived flour, (iv) at least 15% plant-derived starch selected from amylose, amylopectin and a combination thereof, (v) a vegetable oil, and (vi) a nutritional supplement comprising a plurality of vitamins and a plurality of minerals, wherein said composition has a water content that is less than or equal to about 30% water by weight, and wherein the product is produced by heat expanded extrusion.

21 Claims, 3 Drawing Sheets

Related U.S. Application Data continuation of application No. PCT/US2018/049202, filed on Aug. 31, 2018.

(60) Provisional application No. 62/632,950, filed on Feb. 20, 2018, provisional application No. 62/553,703, filed on Sep. 1, 2017.

(51) Int. Cl.
| | |
|---|---|
| *C07K 14/37* | (2006.01) |
| *C07K 14/395* | (2006.01) |
| *C07K 14/38* | (2006.01) |
| *A23K 20/158* | (2016.01) |
| *A23K 10/18* | (2016.01) |
| *A23K 40/00* | (2016.01) |
| *A23J 1/00* | (2006.01) |

(52) U.S. Cl.
CPC .......... *A23K 20/158* (2016.05); *A23K 40/00* (2016.05); *C07K 14/37* (2013.01); *C07K 14/38* (2013.01); *C07K 14/395* (2013.01)

(58) Field of Classification Search
USPC .......................................................... 426/61
See application file for complete search history.

(56) References Cited

U.S. PATENT DOCUMENTS

| | | | |
|---|---|---|---|
| 3,876,793 A | 4/1975 | Salvesen et al. | |
| 3,939,284 A | 2/1976 | Akin et al. | |
| 4,330,463 A | 5/1982 | Luijerink et al. | |
| 4,731,248 A * | 3/1988 | Hogan | A23K 50/42 426/54 |
| 4,800,093 A | 1/1989 | Hogan et al. | |
| 4,960,589 A | 10/1990 | Sasagawa | |
| 5,283,059 A | 2/1994 | Suzuki et al. | |
| 6,338,866 B1 * | 1/2002 | Criggall | A23K 10/16 426/53 |
| 8,672,245 B2 | 3/2014 | Finnigan et al. | |
| 9,309,545 B2 | 4/2016 | Medoff | |
| 9,700,067 B2 | 7/2017 | Fraser et al. | |
| 2002/0054935 A1 | 5/2002 | Yamamoto et al. | |
| 2003/0157219 A1 * | 8/2003 | Bijl | A23J 1/008 426/49 |
| 2007/0092632 A1 | 4/2007 | Kubow et al. | |
| 2007/0251465 A1 * | 11/2007 | Shafer | A01K 5/0114 119/497 |
| 2008/0299286 A1 | 12/2008 | Josephson et al. | |
| 2011/0183036 A1 * | 7/2011 | Teconchuk | A23K 40/20 426/61 |
| 2012/0231114 A1 | 9/2012 | Bezerra De Oliveira et al. | |
| 2014/0288193 A1 | 9/2014 | Hansen et al. | |
| 2015/0175947 A1 | 6/2015 | Menon et al. | |
| 2015/0305390 A1 | 10/2015 | Vrljic et al. | |
| 2016/0073671 A1 | 3/2016 | Geistlinger et al. | |
| 2016/0326484 A1 * | 11/2016 | Jewell | C12N 1/16 |
| 2017/0105438 A1 | 4/2017 | Ajami et al. | |
| 2017/0188612 A1 | 7/2017 | Varadan et al. | |
| 2017/0258125 A1 | 9/2017 | Thomas | |
| 2019/0069575 A1 | 3/2019 | Shigeta et al. | |

FOREIGN PATENT DOCUMENTS

| | | |
|---|---|---|
| CN | 103073351 A | 5/2013 |
| CN | 103073351 B | 7/2015 |
| CN | 105211555 A | 1/2016 |
| CN | 105265762 A | 1/2016 |
| CN | 105614025 A | 6/2016 |
| CN | 105961513 A | 9/2016 |
| GB | 928636 A | 6/1963 |
| WO | WO-0015045 A1 | 3/2000 |
| WO | WO-2015048339 A2 | 4/2015 |
| WO | WO-2018185318 A1 | 10/2018 |
| WO | WO-2019046782 A2 | 3/2019 |

OTHER PUBLICATIONS

Taste of Home, "Savory mushroom bread", [online] Accessed Dec. 21, 2018 fromhttps://www.tasteofhome.com/recipes/savory-mushroom-bread/ (3 pgs).

Chauhan et al. Bioconversion of Low Quality Lignocellulosic Agricultural waste into Edible Protein by Pleurotus djamor (Rumph) Boedijn. International Journal of bioresource and Stress Management 6(1):135-139 (2015).

Everything Old Is New Again—Dried Yeast. ADM Animal Nutrition—Versity. Available at ADMAnimalNutrition.com/Pet (1 pg) (2017).

Nasseri et al. Single Cell Protein: Production and Process. American Journal of Food Technology 6(2):103-116 (2011).

PCT/US2018/049202 International Search Report and Written Opinion dated Apr. 9, 2019.

U.S. Appl. No. 16/133,619 Office Action dated Apr. 8, 2019.

U.S. Appl. No. 16/133,619 Office Action dated Nov. 29, 2018.

Contraplex Pin Mills. Type 160 c to 1120 CW Brochure. Hosokawa Alpine Aktiengesellschaft—http:www.alpinehosokawal.com (6 pls) (2019).

Search and Examination Report under Section 17 dated Dec. 21, 2018, for GB application No. 1816292.5.

* cited by examiner

PROTEIN-CONTAINING COMPOSITIONS

BACKGROUND

Demands for high-quality proteins are expected to rapidly increase as the global population increases exponentially. Animal-sourced proteins are a main source of high-quality dietary protein. Production of animal-sourced proteins is an environmentally demanding process, raising concerns about the sustainability and environmental impact of animal agriculture. Production of animal-sourced proteins is also a resource intensive process. Alternative protein sources to animal-based proteins may greatly reduce the environmental and resource impact of food production. For example, approximately six to seventeen times more land, four to twenty-six times more water, and eleven times more fossil energy are needed to produce animal-sourced protein than the commensurate amount of plant-sourced protein. The environmental and resource cost of single cell or microbial-sourced protein may be even less than that of plant-based protein, with plant-based protein requiring approximately one hundred times the amount of land and five times the amount of water to produce an equal amount of protein.

SUMMARY

The present disclosure provides methods of producing and compositions of single-cell food products for human and animal consumption. The food products described herein may be produced from edible, single celled microorganisms such as fungal, bacterial, algal, or synthetic mammalian or animal cells and may include other ingredients for flavor, preservation, nutrition, and palatability.

In an aspect, the present disclosure provides a method for producing a food product for animal consumption, comprising combining at least (i) a fungus-containing product and (ii) one or more members selected from the group consisting of a flour, an oil, a flavoring agent, and a nutritional supplement, to form a mixture, wherein the mixture comprises the fungus-containing product at greater than or equal to about 3% by wet weight; and heating the mixture at a temperature of greater than or equal to about 150° C. at an ambient pressure for a period of time of at least about 10 seconds, thereby generating the food product for animal consumption, wherein the food product has a water content of less than or equal to about 30% by weight. In some embodiments, the food product is not cheese, a cheese-containing product, cheese replica, or synthetic cheese. In some embodiments, the food product is not derived from cheese.

In some embodiments, the method further comprises providing a reactor comprising (i) a fungal colony and (ii) a feedstock comprising a nitrogen-containing material and a sugar-containing material, and permitting the fungal colony to grow in presence of the feedstock to yield the fungus-containing product. In some embodiments, the fungal colony grows in absence of a support media. In some embodiments, the sugar-containing material includes one or more members selected from the group consisting of (i) a sugar, (ii) a soft agricultural waste, and (iii) a hard agricultural waste. In some embodiments, the fungal colony comprises one or more fungi selected from the group consisting of *Aspergillus oryzae, Fusarium venenatum, Geotrichum candidum, Penicillium camemberti, Penicillium roqueforti*, and a derivative thereof.

In some embodiments, the fungus-containing product comprises one or more fungi selected from the group consisting of *Aspergillus oryzae, Fusarium venenatum, Geotrichum candidum, Penicillium camemberti, Penicillium roqueforti, Saccharomyces cerevisiae*, and a derivative thereof. In some embodiments, the fungus-containing product is *Aspergillus oryzae*. In some embodiments, the fungus-containing product is *Aspergillus oryzae* and *Saccharomyces cerevisiae*. In some embodiments, the *Aspergillus oryzae* and *Saccharomyces cerevisiae* are present at an *Aspergillus oryzae* to *Saccharomyces cerevisiae* ratio from about 1:5 to 1:2.

In some embodiments, the fungus-containing product is a whole cell product. In some embodiments, the fungus-containing product is a protein concentrate containing from about 60% to 90% protein by dry weight. In some embodiments, the fungus-containing product is a protein isolate containing at least about 90% protein by dry weight. In some embodiments, an amount of the fungus-containing product in the food product is at least about 30% by dry weight. In some embodiments, the amount is at least about 50% by dry weight. In some embodiments, the amount is at least about 60% by dry weight.

In some embodiments, the food product does not contain an animal protein. In some embodiments, the food product does not contain an animal oil. In some embodiments, the water content is from about 15% to 30% by weight. In some embodiments, the water content is less than or equal to about 15% by weight. In some embodiments, the temperature is greater than or equal to about 175° C. In some embodiments, the period of time is greater than or equal to about 10 minutes. In some embodiments, the nutritional supplement includes a vitamin supplement or mineral supplement.

In some embodiments, the fungus-containing product is not added to the mixture or the food product as a spray or a coating. In some embodiments, heating the mixture at the temperature of greater than or equal to about 150° C. for the period of time yields an intermediate product, which intermediate product is subjected to one or more processes to yield the food product.

In another aspect, the present disclosure provides a method for producing a food product for animal consumption, comprising providing a reactor comprising (i) a fungal colony and (ii) a feedstock comprising a nitrogen-containing material and a sugar-containing material; permitting the fungal colony to grow in presence of the feedstock to yield a fungus-containing product, wherein the fungus-containing product is not treated to reduce a concentration of ribonucleic acids (RNA); and combining the fungus-containing product with one or more members selected from the group consisting of a flour, an oil, a flavoring agent, and a nutritional supplement, thereby generating the food product for animal consumption, wherein the food product comprises greater than or equal to about 3% by wet weight of the fungus-containing product, and wherein the food product does not contain an animal protein. In some embodiments, the food product is not cheese, a cheese-containing product, cheese replica, or synthetic cheese. In some embodiments, the food product is not derived from cheese.

In some embodiments, the fungal colony grows in absence of a support media. In some embodiments, the fungus-containing product is not added to the food product as a spray or coating. In some embodiments, the sugar-containing material includes one or more members of the group consisting of (i) a sugar, (ii) a soft agricultural waste, and (iii) a hard agricultural waste. In some embodiments, the fungal colony comprises one or more fungi selected from the group consisting of *Aspergillus oryzae, Fusarium venenatum, Geotrichum candidum, Penicillium camemberti, Peni-*

*cillium roqueforti*, and a derivative thereof. In some embodiments, the fungal colony is *Aspergillus oryzae*. In some embodiments, the fungus-containing product is *Aspergillus oryzae* and *Saccharomyces cerevisiae*. In some embodiments, the *Aspergillus oryzae* and *Saccharomyces cerevisiae* are present at an *Aspergillus oryzae* to *Saccharomyces* ratio from about 1:5 to 1:2.

In some embodiments, the fungus-containing product is a whole cell product. In some embodiments, the fungus-containing product is a protein concentrate containing from about 60% to 90% protein by dry weight. In some embodiments, the fungus-containing product is a protein isolate containing at least about 90% protein by dry weight. In some embodiments, an amount of the fungus-containing product in the food product is at least about 30% by dry weight. In some embodiments, the amount is greater than or equal to about 50% by dry weight. In some embodiments, the amount is at least about 60% by dry weight.

In some embodiments, the food product does not contain an animal oil. In some embodiments, the concentration of RNA in the fungus-containing food product is greater than or equal to about 4% by dry weight. In some embodiments, the concentration of RNA in the fungus-containing food product is greater than or equal to about 6% by dry weight. In some embodiments, the nutritional supplement includes a vitamin supplements or mineral supplement. In some embodiments, the method further comprises heating the fungus-containing produce and the one or more member selected from the group consisting of the flour, oil, flavoring agent, and nutritional supplement at a temperature of greater than or equal to about 150° C. at an ambient pressure for a period of time of at least about 10 seconds to reduce a water content of the food product.

In another aspect, the present disclosure provides a method for producing a product for animal consumption, comprising providing a reactor comprising (i) a fungal colony, wherein the fungal colony comprises one or more fungi selected from the group consisting of *Aspergillus oryzae, Fusarium venenatum, Geotrichum candidum, Penicillium camemberti, Penicillium roqueforti*, and a derivative thereof, and (ii) a feedstock comprising a nitrogen-containing material and a sugar-containing material; and permitting the fungal colony to grow in presence of the feedstock, to yield the fungus-containing product, which fungus-containing product is generated at a rate such that a volume of the fungal colony at least doubles in a time period of at most 90 minutes.

In some embodiments, the reactor is a chemostat reactor. In some embodiments, the chemostat reactor further comprises an influent stream, an effluent stream, and a recycle stream, which recycle stream directs recycle from the effluent stream to the influent stream. In some embodiments, the influent stream comprises the nitrogen-containing material and the sugar-containing material. In some embodiments, the effluent stream is separated into the fungal colony and a liquid media. In some embodiments, the recycle stream comprises the liquid media. In some embodiments, the reactor is seeded with a seed culture that is from about 0.1% to 10% of a volume of the reactor. In some embodiments, the reactor is operated at a temperature from about 20° C. to 40° C. In some embodiments, the method further comprises regulating and modulating the temperature in response to an amount of the fungus-containing product in the effluent stream.

In some embodiments, the sugar-containing material includes one or more members selected from the group consisting of (i) a sugar, (ii) a soft agricultural waste, and (iii) a hard agricultural waste. In some embodiments, the sugar-containing material does not include a purified sugar. In some embodiments, the sugar-containing material has a lignin content of less than or equal to about 10% by dry weight. In some embodiments, the sugar-containing material is pretreated to remove the lignin. In some embodiments, the lignin content is 0%. In some embodiments, the method further comprises providing a polyol to the reactor. In some embodiments, the nitrogen-containing material comprises a nitrate salt, an ammonia salt, a urea compound, nitrogen gas, ammonium hydroxide, or any combination thereof.

In some embodiments, the fungus-containing product is a whole cell product. In some embodiments, the method further comprises extracting and purifying protein from the fungus-containing product. In some embodiments, the fungus-containing product is a protein concentrate containing from about 60% to 90% protein by dry weight. In some embodiments, the fungus-containing product is a protein isolate containing greater than or equal to about 90% protein by dry weight. In some embodiments, the method further comprises combining the fungus-containing product with one or more members selected from the group consisting of a flour, an oil, a flavoring agent, and a nutritional supplement to generate the food product. In some embodiments, the method further comprises heating the fungus-containing product and the one or more members selected from the group consisting of the flour, the oil, the flavoring agent, and the nutritional supplement at a temperature of greater than or equal to about 150° C. at an ambient pressure for a period of time of at least about 10 seconds to reduce a water content of the food product.

In some embodiments, the method further comprises providing the fungus-containing product for use in a food product, which food product is suitable for consumption. In some embodiments, the food product is suitable for human consumption. In some embodiments, the food product is suitable for animal consumption. In some embodiments, the animal is a dog, cat, goat, pig, or rodent (e.g., rat or mouse). In some embodiments, an amount of the fungus-containing product in the food product is at least about 30% by dry weight. In some embodiments, the amount is at least about 50% by dry weight. In some embodiments, the amount is at least about 60% by dry weight.

In some embodiments, the fungal colony is selected for a high growth rate. In some embodiments, the fungal colony is selected for an ability to uptake nitrate salts, ammonia salts, or urea compounds and produce biomass. In some embodiments, the fungal colony is selected for an ability to uptake soft agricultural waste and produce biomass. In some embodiments, the fungal colony is selected for an ability to uptake hard agricultural waste and produce biomass. In some embodiments, the fungal colony has a highest sporulation efficiency as compared to other fungal colonies.

In some embodiments, the fungal colony is co-cultured with a bacterial colony. In some embodiments, the bacterial colony comprises one or more bacteria selected from the group consisting of *Bifidobacterium bifidum, Lactobacillus acidophilus, Lactobacillus casei, Lactobacillus delbrueckii* subspecies *bulgaricus, Lactobacillus rhamnosus Streptococcus thermophiles*, and a derivative thereof.

In another aspect, the present disclosure provides a food product for animal consumption, comprising, (i) protein at a protein content of at least about 16% by dry weight, wherein at least about 50% by dry weight of the protein has an amino acid sequence encoded by one or more fungal genomes, and (ii) one or more members selected from the group consisting of a flour, an oil, a flavoring agent, and a nutritional supplement, wherein the food product has a water content that is less than or equal to about 30% water by weight. In some embodiments, the food product is not cheese, a cheese-containing product, cheese replica, or synthetic cheese. In some embodiments, the food product is not derived from cheese.

In some embodiments, the food product comprises at least 30% fungal cells by dry weight comprising at least a subset of the protein comprising the amino acid sequence encoded by one or more fungal genomes. In some embodiments, the fungal cells are not disposed on a surface of a support media. In some embodiments, the fungal cells comprise cells from one or more of *Aspergillus oryzae, Fusarium venenatum, Geotrichum candidum, Penicillium camemberti, Penicillium roqueforti, Saccharomyces cerevisiae*, and a derivative thereof. In some embodiments, the fungal cells comprises *Aspergillus oryzae* and *Saccharomyces cerevisiae*. In some embodiments, the *Aspergillus oryzae* and the *Saccharomyces cerevisiae* are present at an *Aspergillus oryzae* to *Saccharomyces cerevisiae* ratio from about 1:5 to 1:2.

In some embodiments, the flour is from about 30% to 50% by dry weight. In some embodiments, the oil is from about 10% to 20% by dry weight. In some embodiments, the food product has a cutting force that is less than about 5 kilogram-force. In some embodiments, the food product has a density of from about 0.3 to 1.3 grams per cubic centimeter. In some embodiments, the water content is from about 15% to 30% by weight. In some embodiments, the water content is less than about 15% by weight. In some embodiments, the protein comprises less than about 50% of proteins comprising amino acid sequences encoded by one or more plant genomes, animal genomes, insect genomes, bacterial genomes, or any combination thereof.

In some embodiments, the nutritional supplement is a vitamin supplement or a mineral supplement. In some embodiments, the food product further comprises a heme-containing protein. In some embodiments, protein comprises an amino acid sequence encoded by one or more bacterial genomes. In some embodiments, the bacterial genome is selected from the group consisting of *Bifidobacterium bifidum, Lactobacillus acidophilus, Lactobacillus casei, Lactobacillus delbrueckii* subspecies *bulgaricus, Lactobacillus rhamnosus Streptococcus thermophiles*, and a derivative thereof.

In some embodiments, the food product has a fibrous structure. In some embodiments, the food product has a shelf life of at least about one year. In some embodiments, the food product has a shelf life of at least about two years.

In another aspect, the present disclosure provides a food product for animal consumption, comprising, (i) greater than or equal to about 3% fungus-containing product by wet weight, wherein the fungus-containing product comprises at least about 4% by dry weight ribonucleic acids encoded by one or more fungal genomes, and (ii) one or more members selected from the group consisting of a flour, an oil, a flavoring agent, and a nutritional supplement, wherein the food product does not contain protein comprising an amino acid sequence encoded by an animal genome. In some embodiments, the food product is not cheese, a cheese-containing product, cheese replica, or synthetic cheese. In some embodiments, the food product is not derived from cheese.

In some embodiments, the fungus-containing product is not part of a coating or an external layer of the food product. In some embodiments, the fungus-containing product comprises one or more of *Aspergillus oryzae, Fusarium venenatum, Geotrichum candidum, Penicillium camemberti, Penicillium roqueforti, Saccharomyces cerevisiae*, and a derivative thereof. In some embodiments, the fungus-containing product comprises *Aspergillus oryzae* and *Saccharomyces cerevisiae*. In some embodiments, the *Aspergillus oryzae* and the *Saccharomyces cerevisiae* are present at an *Aspergillus oryzae* to *Saccharomyces cerevisiae* ratio form about 1:5 to 1:2.

In some embodiments, the fungus-containing product comprises at least 6% by dry weight ribonucleic acids encoded by one or more fungal genomes. In some embodiments, the flour is from about 30% to 50% by dry weight. In some embodiments, the oil is from about 10% to 20% by dry weight. In some embodiments, the food product has a cutting force that is less than about 5 kilogram-force. In some embodiments, the food product has a density of from about 0.3 to 1.3 grams per cubic centimeter. In some embodiments, an amount of the fungus-containing product in the food product is at least about 30% by dry weight. In some embodiments, the amount is at least about 50% by dry weight. In some embodiments, the amount is at least about 60% by dry weight.

In some embodiments, the fungus-containing product is a whole cell product. In some embodiments, the nutritional supplement is a vitamin supplement or mineral supplement. In some embodiments, the food product further comprises a heme-containing protein. In some embodiments, the food product further comprises a bacteria-containing product. In some embodiments, the bacteria-containing product is derived from one or more bacteria selected from the group consisting of *Bifidobacterium bifidum, Lactobacillus acidophilus, Lactobacillus casei, Lactobacillus delbrueckii* subspecies *bulgaricus, Lactobacillus rhamnosus Streptococcus thermophiles*, and a derivative thereof.

In some embodiments, the food product has a fibrous structure. In some embodiments, the food product has a shelf life of at least one year. In some embodiments, the food product has a shelf life of at least two years.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed descrip

DETAILED DESCRIPTION

Figure 1:
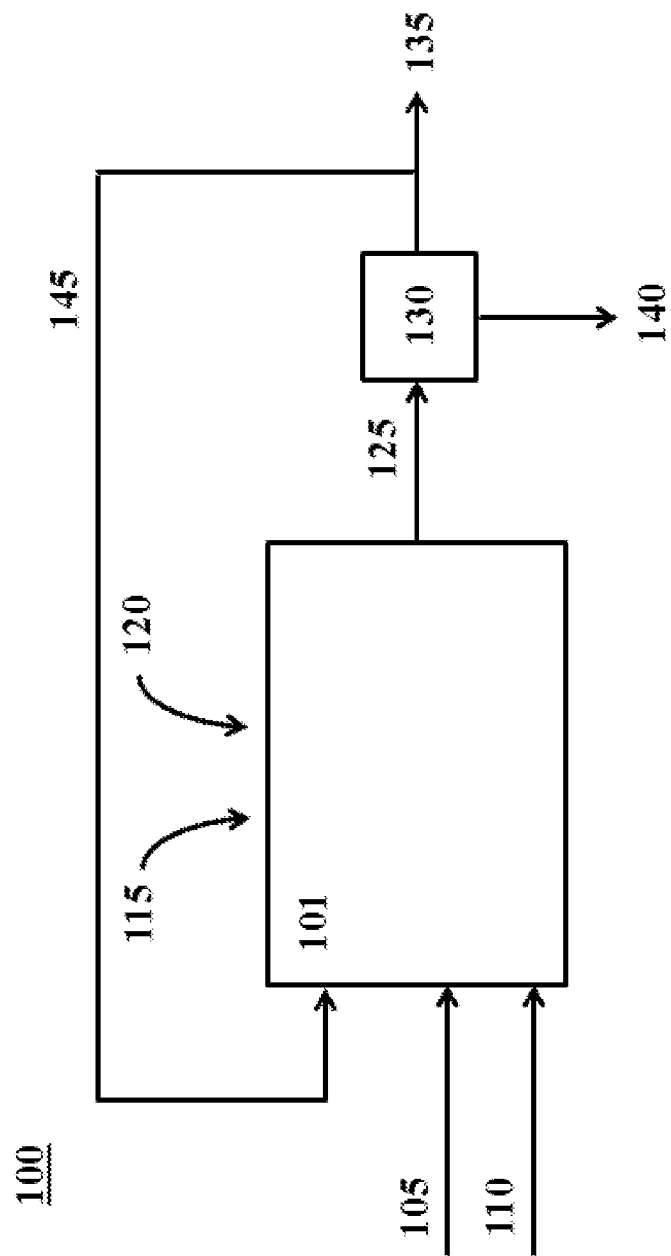
- FIG. 1 shows an example of a system for producing single-cell protein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "single-cell protein" and "microbial protein," as used herein, generally refer to an edible unicellular microorganisms (e.g., edible biomass) containing protein. The unicellular microorganism may be fungi, yeast, algae, bacteria, synthetically grown mammalian cells, or synthetically grown animal cells. The single-cell protein may be a whole cell or a protein extracted from a whole cell. Single-cell protein may contain from about 10% to 80% protein on a dry matter basis (e.g., by dry weight). For example, a single-cell protein having a mass of $10^{12}$ nanograms may have a total protein mass of about $5 \times 10^{-13}$ nanograms, in which case the protein content of the single-cell protein is 50% by dry weight.

The term "whole cell," as used herein, generally refers to the entirety of a unicellular organism. For example, a whole cell may include the cell membrane, cytoplasm, cell wall, and nucleus of a cell. The whole cell may be non-processed such that the cell membrane and cell wall are intact. Alternatively, or in addition to, the whole cell may be processed to lyse the cells. Processing may include homogenizing, sonication, mechanical grinding, or chemical treatment. The whole cell product may not be purified, filtered, or otherwise processed to remove cellular components.

The term "protein concentrate," as used herein, generally refers to protein derived from a unicellular organism that has been extracted from the unicellular organism and purified. Protein concentrate may comprise greater than or equal to about 40%, 50%, 60%, 70%, or 80%, or more total protein on a dry matter basis. The protein concentration of the protein concentrate may be increased by greater than or equal to about 20%, 30%, 40%, 50%, 60%, 70%, 80%, or more than the protein concentration of the source unicellular organism (e.g., whole cell). A protein concentrate may comprise a single type of protein or a combination of different types of proteins. Protein in a protein concentrate may be derived from a single type of unicellular organism or the protein concentrate may be derived from a mixture of different unicellular organisms.

The term "protein isolate," as used herein, generally refers to protein derived from a unicellular organism that has been extracted from the organism and purified. A protein isolate may have a higher purity than a protein concentrate. A protein isolate may be formed by further processing a protein concentrate to increase the protein concentration. Protein isolate may comprise greater than or equal to about 80%, 90%, 95%, or more protein on a dry matter basis. A protein isolate may comprise a single type of protein or a combination of different types of proteins. Protein in a protein isolate may be derived from a single type of unicellular organism or the protein isolate may be derived from a mixture of different unicellular organisms.

The term "dry matter basis" and "dry weight," as used herein, generally refer to a measurement of the mass of a material when completely dried. The dry matter or dry weight of a plant, animal, or microorganism may be the solid constituent portion of the material (e.g., excluding water).

The term "wet matter basis" and "wet weight," as used herein, generally refer to a measurement of the mass of a material in a non-dried state. The wet matter or wet weight of plant, animal, or microorganism materials may be the solid and liquid constituent portions of the material (e.g., material including water).

The term "reactor," as used herein, generally refers to any system containing microorganisms, in which materials are converted by the microorganisms, products are produced by the microorganisms, or in which an increase in cell population is achieved. Reactors may be one or more of batch reactors, fed-batch reactors, semi-continuous reactors, continuous stirred-tank reactors, continuous flow stirred-tank reactors, or plug-flow reactors. The reactor may be a singular reactor or comprise multiple reactors in a series or parallel configuration. The reactor may have one or more inputs (e.g., influent streams or operating controls) and/or one or more outputs (e.g., effluent streams). One or more of the effluent streams may be recycled back to one or more of the influent streams.

The term "support media," as used herein, generally refers to any structure on which a unicellular organism may grow. The structure may include synthetic or organic structures. The support media may be a media that is inert (e.g., not consumed by) the unicellular organism or a media that is consumed by the unicellular organism. Example synthetic structures may include, but are not limited to, silica or polymer based particles, substrates, or features configured to support microorganism growth. Synthetic support media may be inert to the growth of unicellular organism. Example organic structures may include, but are not limited to, grains, seed, or other starch substrates capable of supporting biomass growth. Organic support media may be at least partially consumed by the unicellular organism during culturing.

The term "nutritional supplement," as used herein, generally refers to a substance capable of supplementing a diet of a subject, such as, for example, a human, dog, cat, or other animal. A nutritional supplement may provide essential nutrients (e.g., vitamins, minerals, macronutrients, trace nutrients, and/or cofactors). A nutritional supplement may be a dietary supplement. Examples of nutritional supplements include, without limitation, taurine and carnitine.

The term "flavoring agent," as used herein, generally refers to a substance capable of altering a flavor of a food product. A flavoring agent may include a flavoring molecule(s) or precursor(s), such as, for example, carbohydrates (e.g., sugar) or salts.

A flavoring agent and the nutritional supplement may be different agents or compounds. As an alternative, the flavoring agent and the nutritional supplement may be the same agent or compound.

Whenever the term "at least," "greater than," or "greater than or equal to" precedes the first numerical value in a series of two or more numerical values, the term "at least," "greater than" or "greater than or equal to" applies to each of the numerical values in that series of numerical values.

For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

Disclosed herein are compositions and methods useful for the production of alternative protein sources. An alternative protein source may be a food product or may be included in a food product. The food product may not be cheese, a cheese-containing product, cheese replica, or synthetic cheese. In some instance, the food product is not derived from cheese.

Alternative protein sources may be incorporated into food products for human and animal consumption. Alternative protein sources may include plant-sourced proteins, insect-sourced proteins, or single-cell proteins. Single-cell proteins may include whole edible unicellular microorganisms or proteins derived from edible unicellular microorganisms. Single-cell proteins may offer a variety of production advantages over animal-sourced and plant-sourced proteins including highly efficient feed conversion, variety of potential feed sources, high productivity, independence from seasonal factors, and lower production costs. Unicellular organisms, which may include fungi, algae, yeast, bacteria, synthetically produced mammalian cells, and synthetically produced animal cells, may contain from about 20% to about 90% protein on a dry matter basis. Single-cell proteins may be incorporated directly into food products as whole cells. Alternatively, or in addition to, single-cell proteins may comprise a protein concentrate or a protein isolate and that protein concentrate or protein isolate may be incorporated into a food product.

Methods for Producing Single-Cell Protein Containing Food Products

In an aspect, the present disclosure provides methods for producing single-cell protein (e.g., microbial protein) containing food products may comprise providing a reactor. The reactor may comprise a unicellular, colony forming organism and a feedstock. The unicellular, colony forming organism may convert the feedstock into biomass. The biomass may be generated at a rate such that the volume of colony forming organism, or total biomass, increases by a factor of at least 100% (e.g., doubles) in less than or equal to about 90 minutes. The biomass may comprise from about 20% to 90% protein on a dry matter basis. The biomass may be incorporated into a protein containing food product. The biomass may be a fungus-containing product, a bacteria-containing product, an algae-containing product, a mammalian cell-containing product, an Animal-containing product, or any combination thereof. The biomass may be a fungal-containing product and the colony forming organism may be a fungal colony that comprises *Aspergillus oryzae, Fusarium venenatum, Geotrichum candidum, Penicillium camemberti, Penicillium roqueforti*, and a derivative thereof.

In another aspect, the present disclosure provides methods for producing a food product. The methods may comprise providing a reactor comprising (i) a fungal colony and (ii) a feedstock comprising a nitrogen-containing material and a sugar-containing material; permitting the fungal colony to grow in the presence of the feedstock to yield a fungus-containing product, where the fungus-containing product is not treated to reduce a concentration of ribonucleic acids (RNA); and combining the fungus-containing product with one or more members selected from the group consisting of a flour, an oil, a flavoring agent, and a nutritional supplement, thereby generating the food product for animal consumption. The food product may comprise greater than or equal to about 3% by wet weight of the fungus-containing product. The food product may or may not contain an animal protein. In an example, the food product does not contain an animal protein. The food product may be for human or animal consumption. In an example, the food product is a treat or kibble for animal consumption.

In another aspect, the present disclosure provides methods for producing a food product. The method may comprise combining at least (i) a fungus-containing product and (ii) one or more members selected from the group consisting of a flour, an oil, a flavoring agent, and a nutritional supplement, to form a mixture. The mixture may comprise the fungus-containing product at greater than or equal to 3% by wet weight. The mixture may be heated at a temperature of greater than or equal to about 150° C. at an ambient pressure for a period of time of at least 10 seconds. The heated mixture may be the food product. The food product may have a water content of less than or equal to about 30% by weight. The food product may be for human or animal consumption. In an example, the food product is a treat or kibble for animal consumption.

Single-cell proteins (e.g., fungal or bacterial proteins) may be different than proteins derived from multicellular organisms (e.g., animal proteins). For example, single-cell proteins may comprise amino acid sequences that are encoded by a microbial genome. Plant proteins may comprise amino acid sequences that are encoded by a plant genome. Animal proteins may comprise amino acid sequences that are encoded by an animal genome. Plant, animal, and microbial proteins may differ in amino acid sequence and bioavailability. Microbial proteins may have similar bioavailability (e.g., digestion rate and adsorption) as many animal proteins. Plant proteins may have lower bioavailability than animal and microbial proteins. A family of proteins may be produced by plants, animals, and microorganisms. For example, a heme-protein may be produced by a plant, animal, or microorganism. The function of the heme-protein may function similarly in plants, animals, and microorganisms, but may have differences in amino acid sequence, size, and structure.

The biomass may be generated from a seed colony and grown to form a biomass-containing product. FIG. 1 shows an example system 100 for producing a biomass-containing product. The biomass-containing product may comprise single-cell protein. The system may comprise a reactor 101 loaded with a seed culture 115 and a liquid media 120. The reactor 101 may have one or more influent streams 105 and 110 that deliver nutrients to the reactor 101. The influent streams may include a sugar-containing stream 105 as a carbon source and a nitrogen-containing stream 110 as a nitrogen source. The reactor may further comprise one or more effluent streams 125. The effluent stream 125 may be directed to a separator 130. The separator 130 may divide the effluent stream 125 into a liquid phase 135 and a solid phase 140. The liquid phase 145 may comprise unused nutrients (e.g., carbon and nitrogen source) and compounds excreted by the biomass. The liquid phase 145 may be recycled back to the reactor. The solid phase 140 may be the biomass or the biomass-containing product. Alternatively, or in addition to, the biomass may be further processed to generate the biomass-containing product.

Figure 2:
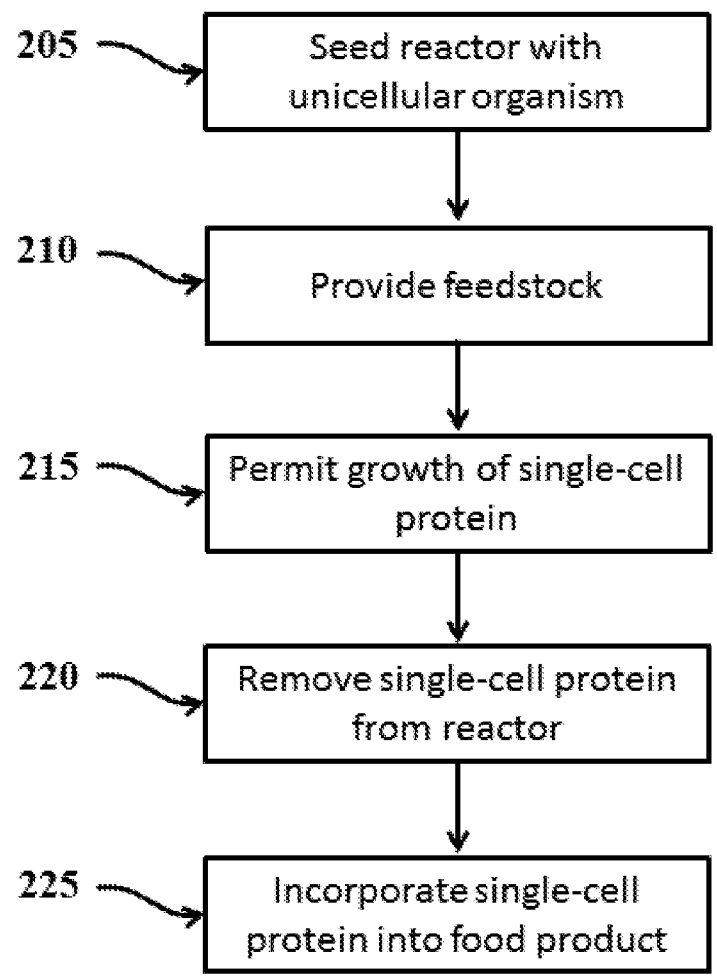
FIG. 2 shows an example of a method for producing single-cell protein.

FIG. 2 shows an example method 200 for producing a biomass-containing product (e.g., single-cell protein or microbial protein) from a reactor system. The reactor may be seeded with a culture of unicellular organisms 205 such as fungi, yeast, bacteria, algae, or synthetically grown animal cells. A feedstock 210 may be provided to the reactor to facilitate production of single-cell protein. The feedstock 210 may contain a sugar-containing material and a nitrogen-containing material. The sugar-containing material may be an agricultural waste (e.g., soft or hard agricultural waste) or a sugar. The nitrogen-containing material may be a nitrate salt, ammonia salt, a urea compound, a pre-digested peptide, nitrogen gas, ammonium hydroxide, or any combination thereof. The unicellular organism may be permitted to grow 215 in the presence of the feedstock to produce a biomass that contains a single-cell protein. The biomass containing the single-cell protein may be removed from the reactor 220 in batches or in a continuous flow mode. The single-cell protein may be incorporated into a food product 225. In one example, the single-cell protein may be purified prior to incorporation into a food product 225.

The reactor may be a batch reactor, semi-batch reactor, continuous stirred-tank reactor (e.g., chemostat reactor), plug flow reactor, or any other reactor type capable for use with microbial fermentation. The reactor may be seeded with a starter culture of unicellular organisms. The starter culture may have a volume that is less than or equal to about 25%, 20%, 15%, 10%, 8%, 6%, 4%, 2%, 1%, 0.5%, 0.1%, or less than the volume of the reactor. The starter culture may have a volume that is greater than or equal to about 0.1%, 0.5%, 1%, 2%, 4%, 6%, 8%, 10%, 15%, 20%, 25%, or greater than the volume of the reactor. The starter culture may have a volume that is from about 0.1% to 5%, 0.1% to 10%, 0.1% to 15% or 0.1% to 20% the volume of the reactor. In an example, the starter culture has a volume that is from about 0.1% to 10% of the volume of reactor.

The starter culture may be added to the reactor during the exponential growth phase. The exponential growth phase may be detected by the optical density (OD) of the starter culture. The OD of the exponential growth phase may be culture specific and may vary for fungi, bacterial, algae, or animal cultures. The wavelength used to detect the OD of the starter culture may be greater than or equal to about 400 nanometers (nm), 450 nm, 500 nm, 550 nm, 600 nm, 650 nm, 700 nm, or more. The wavelength used to detect the OD of the starter culture may be less than or equal to about 700 nm, 650 nm, 600 nm, 550 nm, 500 nm, 450 nm, 400 nm, or less. The wavelength used to detect the OD of the starter culture may be from about 400 nm to 450 nm, 400 nm to 500 nm, 400 nm to 550 nm, 400 nm to 600 nm, 400 nm to 650 nm, or 400 nm to 700 nm. In an example, the wavelength is from 550 nm to 600 nm, 575 nm to 625 nm, or 600 nm to 650 nm. The starter culture may be added to the reactor when the OD is greater than or equal to 0.1, 0.2, 0.3, 0.4, 0.5, 0.6, 0.7, 0.8, 0.9, 1.0, 1.2, 1.5, or more. The starter culture may be added to the reactor when the OD is less than or equal to 1.5, 1.2, 1.0, 0.9, 0.8, 0.7, 0.6, 0.5, 0.4, 0.3, 0.2, 0.1, or less. The starter culture may be added to the reactor when the OD is from 0.1 to 0.2, 0.1 to 0.3, 0.1 to 0.4, 0.1 to 0.5, 0.1 to 0.6, 0.1 to 0.7, 0.1 to 0.8, 0.1 to 0.9, 0.1 to 1.0, 0.1 to 1.2, or 0.1 to 1.5. In an example, the starter culture is added to the reactor when the OD is from 0.5 to 1.0.

The seed culture may contain a single species of unicellular organisms or a consortium of unicellular organisms. Microbial proteins may be extracted from the unicellular organisms or the unicellular organisms may be used as whole cells. The unicellular organisms used to make a food product may be fungi, yeast, bacteria, algae, or synthetically produced animal (e.g., mammalian) cells. The unicellular organisms may be any yeast or fungi used to produce a food product or consumed as a food. Fungi and yeast used to make a food product may include, but is not limited to, *Aspergillus acidus*, *Aspergillus niger*, *Aspergillus fumigatus*, *Aspergillus oryzae*, *Aspergillus sojae*, *Candida colliculosa*, *Candida exiguous*, *Candida humicola*, *Candida kefyr*, *Candida krusei*, *Candida mycoderma*, *Candida pelliculosa*, *Candida rugose*, *Candida tropicalis*, *Candida utilis*, *Candida valida*, *Candida vini*, *Candida zeylanoides*, *Cyberlindnera mrakii*, *Cystofilobasidium infirmominiatum*, *Debaryomyces hansenii*, *Debaryomyces kloeckeri*, *Fusarium domesticum*, *Fusarium venenatum*, *Geotrichum candidum*, *Issatchenkia orientalis*, *Kazachstania unispora*, *Kloeckera africana*, *Dloeckera apis*, *Kloeckera javanica*, *Kluyveromyces lactis*, *Kluyveromyces marxianus*, *Lecanicillium lecanii*, *Mucor hiemalis*, *Mucor plumbeus*, *Mucor racemosus*, *Neurospora intermedia*, *Penicillium album*, *Penicillium camemberti*, *Penicillium caseifulvum*, *Penicillium chrysogenum*, *Penicillium nalgiovense*, *Penicillium roqueforti*, *Penicillium solitum*, *Pichia fermentans*, *Rhizopus microspores*, *Rhodosporidium infirmominiatum*, *Rhodotorula glutinis*, *Rhodotorula minuta*, *Rhodotorula rubra*, *Saccharomyces bayanus*, *Saccharomyces calsbergensis*, *Saccharomyces cerevisiae*, *Saccharomyces pastorianus*, *Saccharomyces rouzii*, *Saccharomyces uvarum*, *Torulaspora delbruenckii*, *Torulopsis versatilis*, *Thrichosporon beigelii*, *Trichoderma longibrachiatum*, *Verticillium lecanii*, *Yarrowia lipolytica*, *Zygotorulaspora florentina*, or any other food safe fungi, yeast, or derivatives thereof. In an example, the fungi may be *Aspergillus oryzae*, *Fusarium venenatum*, *Geotrichum candidum*, *Penicillium camemberti*, *Penicillium roqueforti*, *Saccharomyces cerevisiae*, or a genetic derivative thereof.

Bacteria used to make a food product may be from the *eubacterium* or *archaebacterium* groups. Bacteria used to make a food product may include, but is not limited to, *Acetobacter aceti*, *Acetobacter cerevisiae*, *Acetobacter fabarum*, *Acetobacter lovaniesis*, *Acetobacter malorum*, *Acetobacter orientalis*, *Acetobacter pasteurianus*, *Acetobacter pomorum*, *Acetobacter syzygii*, *Acetobacter tropicalis*, *Arthrobacter arilaitensis*, *Arthrobacter bergerei*, *Arthrobacter globiformis*, *Arthrobacter nicotianae*, *Arthrobacter variabilis*, *Bacillus cereus*, *Bacillus coagulans*, *Bacillus lentus*. *Bacillus licheniformis*, *Bacillus pumilus*, *sphaericus*, *Bacillus stearothermophilus*, *Bacillus subtilis*, *Bacteroides amylophilus*, *Bacteroides capillosus*, *Bacteroides ruminocola*, *Bacteroides suis*, *Bifidobacterium adolescentis*, *Bifidobacterium animalis*, *Bifidobacterium bifidum*, *Bifidobacterium breve*, *Bifidobacterium infantis*, *Bifidobacterium lactis*, *Bifidobacterium logum*, *Bifidobacterium pseudolongum*, *Bifidobacterium thermophilum*, *Brachybacterium alimentarium*, *Brachybacterium tyrofermentans*, *Brevibacterium aurantiacum*, *Brevibacterium casei*, *Brevibacterium lines*, *Carnobacterium divergens*, *Carnobacterium maltaromatiucum*, *Carnobacterium piscicola*, *Corynebacterium ammoniagenes*, *Corynebacterium casei*, *Corynebacterium flavescens*, *Corynebacterium mooreparkense*, *Corynebacterium variabile*, *Enterococcus cremoris*, *Enterococcus diacetylactis*, *Enterococcus faecalis*, *Enterococcus faecium*, *Enterococcus intermedius*, *Enterococcus lactis*, *Enterococcus thermophilus*, *Gluconacetobacter azotocaptans*, *Gluconacetobacter diazotrophicus*, *Gluconacetobacter entanii*, *Gluconacetobacter europaeus*, *Gluconacetobacter hansenii*, *Gluconacetobacter johannae*, *Gluconacetobacter oboediens*, *Gluconacetobacter xylinus*, *Gluconobacter oxydans*, *Hafnia alvei*, *Halomonas elongata*,

*Kocuria rhizophila, Kocuria varians, Lactobacillus acetotolerans, Lactobacillus acidifarinae, Lactobacillus acidophilus, Lactobacillus acidipiscis, Lactobacillus alimentarius, Lactobacillus brevis, Lactobacillus bucheri, Lactobacillus bulgaricus, Lactobacillus cacaonum, Lactobacillus casei, Lactobacillus cellobiosus, Lactobacillus curvatus, Lactobacillus collinoides, Lactobacillus composti, Lactobacillus coryniformis, Lactobacillus crispatus, Lactobacillus curvatus, Lactobacillus delbruenckii, Lactobacillus dextrinicus, Lactobacillus diolivorans, Lactobacillus fabifermentans, Lactobacillus farciminis, Lactobacillus fermentum, Lactobacillus gasseri, Lactobacillus ghanensis, Lactobacillus hammesii, Lactobacillus harbinensis, Lactobacillus helveticus, Lactobacillus hilgardii, Lactobacillus homohiochii, Lactobacillus jensenii, Lactobacillus johnsonii, Lactobacillus kefiranofaciens, Lactobacillus kimchi, Lactobacillus kisonensis, Lactobacillus kunkeei, Lactobacillus lactis, Lactobacillus mali, Lactobacillus manihotivorans, Lactobacillus mindensis, Lactobacillus mucosae, Lactobacillus nagelii, Lactobacillus namuresis, Lactobacillus nantesis, Lactobacillus nodensis, Lactobacillus oeni, Lactobacillus otakiensis, Lactobacillus panis, Lactobacillus parabrevis, Lactobacillus parabuchneri, Lactobacillus paracasei, Lactobacillus parakefiri, Lactobacillus paralimentarius, Lactobacillus pentosus, Lactobacillus perolens, Lactobacillus plantarum, Lactobacillus pobuzihii, Lactobacillus pontis, Lactobacillus rapi, Lactobacillus reuteri, Lactobacillus rhamnosus, Lactobacillus rossiae, Lactobacillus sakei, Lactobacillus salivarius, Lactobacillus sanfranciscensis, Lactobacillus satsumensis, Lactobacillus secaliphilus, Lactobacillus senmaizukei, Lactobacillus siliginis, Lactobacillus similis, Lactobacillus spicheri, Lactobacillus suebicus, Lactobacillus sunkii, Lactobacillus tucceti, Lactobacillus vaccinostercus, Lactobacillus versmoldesis, Lactobacillus yamanashiensis, Lactococcus lactis, Lactococcus raffinolactis, Lecanicillium lecanii, Leuconostoc carnosum, Leuconostoc citreum, Leuconostoc fallax, Leuconostoc holzapefelii, Leuconostoc inhae, Leuconostoc kimchi, Leuconostoc lactis, Leuconostoc mesenteroides, Leuconostoc palmae, Leuconostoc pseudomesenteroides, Macrococcus caseolyticus, Microbacterium foliorum, Microbacterium gubbeenense, Micrococcus luteus, Micrococcus lylae, Oenocuccus oeni, Pediococcus acidilactici, Pediococcus cerevisiae, Pediococcus pentosaceus, Propionibacterium acidipropionici, Propionibacterium freudenreichii, Propionibacterium jensenii, Propionibacterium shermanii, Propionibacterium thoenii, Proteus vulgaris, Pseudomonas fluorescens, Psychrobacter celer, Staphylococcus carnosus, Staphylococcus condiment, Staphylococcus equorum, Staphylococcus fleurettii, Staphylococcus piscifermentans, Staphylococcus saphrophyticus, Staphylococcus sciuri, Staphylococcus simulans, Staphylococcus succinus, Staphylococcus vitulinus, Staphylococcus warneri, Staphylococcus xylosus, Streptococcus gallolyticus, Streptococcus salivarius, Streptococcus thermophiles, Streptomyces griseus, Streptomyces mobaraensis, Tetragenococcus halophilus, Tetragenococcus koreensis, Weissella beninensis, Weissella cibaria, Weissella fabaria, Weissella ghanesis, Weissella koreensis, Weissella paramesenteroides, Weissella thailandensis, Zymomonas mobilis*, or any other food safe bacterium or derivatives thereof. In an example, the bacteria may include *Bifidobacterium bifidum, Lactobacillus acidophilus, Lactobacillus casei, Lactobacillus delbrueckii* subspecies *bulgaricus*, and *Lactobacillus rhamnosus Streptococcus thermophiles*, and a derivative thereof.

Algae used to make a food product may include, but is not limited to, species from the genera *Chlorella, Tetraselmis, Spirulina, Nannochloropsis, Nitzchia, Navicula, Chaetoceros, Scenedesmus, Haematococcus, Ulva, Monostroma, Laminaria, Undaria, Hizikia, Himanthalia, Eisenia, Ascophyllum, Fucus, Porphyra, Cladophora, Microspora, Palmaria*, or any other food safe algae or derivatives thereof.

In an example, the food product comprises one or more unicellular organisms. The one or more unicellular organisms may be of the same type (e.g., all fungi) or of different types (e.g., fungi and bacteria). The unicellular organisms may be cultured in a single reactor (e.g., co-cultured) or cultured in multiple reactors (e.g., cultured separately). In an example, the food product contains one or more fungi selected from the group consisting of *Aspergillus oryzae, Fusarium venenatum, Geotrichum candidum, Penicillium camemberti, Penicillium roqueforti, Saccharomyces cerevisiae*, and a derivative thereof. In an example, the food product contains one or more bacteria selected from the group consisting of *Bifidobacterium bifidum, Lactobacillus acidophilus, Lactobacillus casei, Lactobacillus delbrueckii* subspecies *bulgaricus, Lactobacillus rhamnosus Streptococcus thermophiles*, and a derivative thereof. In an example, the food product contains both fungal and bacterial cultures and the fungal and bacterial cultures are co-cultured. In an example, the food product comprises *Aspergillus oryzae, Saccharomyces cerevisiae*, or both *Aspergillus oryzae* and *Saccharomyces cerevisiae*.

The food product may include synthetically grown mammalian cells or other animal cells. The synthetically grown mammalian cells or animal cells may be replicated in a culture outside of an animal and incorporated into a food product. The food product may contain proteins completely derived from mammalian cells or animal cell, such as animal or insect proteins, or the food product may contain proteins derived from mammalian cells, animal cells, or proteins derived from other unicellular organisms. The synthetically grown mammalian cells or animal cell may be derived from livestock, poultry, fish, or insects. The synthetically grown mammalian cells or animal cells may be incorporated into the food product as whole cells, protein concentrates, or protein isolates.

The food product may be derived from a single unicellular organism or may be derived from a consortium of unicellular organisms. The consortium of unicellular organisms may be fermented individually or may be fermented as a co-culture. The food product may be derived from one or more strains from one or more different organisms. The one or more strains and one or more different organisms may be fermented individually or as a co-culture. In an example, the food product is derived from a co-culture fermentation of one or more fungal species and one or more bacterial species. Unicellular organisms produced as a co-culture may include fungal organisms, bacterial organisms, algal organisms, animal cells, or any combination thereof. A co-culture may include a single strain of each organism in the co-culture or multiple strains from each organism in the co-culture. In an example, one or more strains of yeast and bacteria are co-cultured to create a food product. A single strain of a unicellular organism may be cultured and, after culturing, another unicellular organism may be added. For example, *Aspergillus oryzae* may be cultured and, after culturing, *Saccharomyces cerevisiae* may be added to generate the food product or a portion of the food product.

The unicellular organism may be selected or engineered for a high growth rate. Selection or engineering of the unicellular organism may include directed evolution or metabolic engineering. Sporulation efficiency may be used to measure and select for high growth rate. Sporulation efficiency may refer to a rate (e.g., numbers of spores per unit time) at which a fungus forms spores. The unicellular organism may have a doubling time (i.e., time for a volume of the unicellular organism to increase by a factor of about 2) that is less than or equal to about 12 hours, 6 hours, 5 hours, 4 hours, 3 hours, 2.5 hours, 2 hours, 1.5 hours, 1 hour, 90 minutes, 80 minutes, 60 minutes, 50 minutes, 40 minutes, 30 minutes, or less. In an example, the unicellular organism (e.g., *Aspergillus oryzae*) has a doubling time of less than 90 minutes. The unicellular organism may increase in volume by at least 50% in at most a 2.5 hour period, by at least 100% in at most a 2.5 hour period, by at least 150% in at most a 2.5 hour period, by at least 200% in at most a 2.5 hour period, by at least 250% in at most a 2.5 hour period, by at least 300% in at most a 2.5 hour period, by at least 400% in at most a 2.5 hour period, by at least 500% in at most a 2.5 hour period, or more in at most a 2.5 hour period. The unicellular organism may increase in volume by at least 50% in at most a 2 hour period, by at least 100% in at most a 2 hour period, by at least 150% in at most a 2 hour period, by at least 200% in at most a 2 hour period, by at least 250% in at most a 2 hour period, by at least 300% in at most a 2 hour period, by at least 400% in at most a 2 hour period, by at least 500% in at most a 2 hour period, or more in at most a 2 hour period. The unicellular organism may increase in volume by at least 50% in at most a 1.5 hour period, by at least 100% in at most a 1.5 hour period, by at least 150% in at most a 1.5 hour period, by at least 200% in at most a 1.5 hour period, by at least 250% in at most a 1.5 hour period, by at least 300% in at most a 1.5 hour period, or more in at most a 1.5 hour period. The unicellular organism may increase in volume by at least 50% in a 1 hour period, by at least 100% in at most a 1 hour period, by at least 150% in at most a 1 hour period, by at least 200% in at most a 1 hour period, by at least 250% in at most a 1 hour period, by at least 300% in at most a 1 hour period, or more in at most a 1 hour period. The selected unicellular organism may be a fungal colony that that increases in volume by at least about 50% in at most a 2.5 hour period, by at least about 50% in at most a 2 hour period, by at least about 50% in at most a 1.5 hour period, by at least about 50% in at most a 1 hour period, by at least about 50% in at most a 30 minute period, by at least about 100% in at most a 2.5 hour period, by at least about 100% in at most a 2 hour period, by at least about 100% in at most a 1.5 hour period, by at least about 100% in at most a 1 hour period, by at least about 100% in at most a 30 minute period, by at least about 200% in at most a 2.5 hour period, by at least about 200% in at most a 2 hour period, by at least about 200% in at most a 1.5 hour period, by at least about 200% in at most a 1 hour period, by at least about 200%, in at most a 30 minute period.

The pH of the reactor may alter or control the growth rate of the unicellular organisms. The reactor may be operated at a pH ranging from about 3 to 3.5, 3 to 4, 3 to 4.5, 3 to 5, 3 to 5.5, 3 to 6, 3 to 6.5, 3 to 7, 3 to 7.5, 3 to 8, or 3 to 8.5. The reactor may be operated at a pH of greater than or equal to about 3, 3.5, 4, 4.5, 5, 5.5, 6, 6.5, 7, 7.5, 8, 8.5, or more. In an example, the unicellular organism is a fungus (e.g., *Aspergillus oryzae*) and the reactor has a pH from 3 to 8 or a pH from 4.5 to 6.5. The reactor may be operated at a temperature ranging from about 20 degrees Celsius (° C.) to 25° C., 20° C. to 30° C., 20° C. to 35° C., or 20° C. to 40° C. The reactor may be operated at a temperature of greater than or equal to about 20° C., 25° C., 30° C., 35° C., 40° C., or greater. The reactor may be operated at a temperature of less than or equal to about 45° C., 40° C., 35° C., 30° C., 25° C., 20° C., or less. In an example, the unicellular organism is a fungus (e.g., *Aspergillus oryzae*) and the reactor is operated at a temperature from 30° C. to 40° C.

The reactor may include one or more influent streams, one or more effluent streams, and/or one or more recycle streams. The influent streams may flow feedstock, an acidic material, and/or a basic material into the reactor. The influent streams may be sterilized to prevent the growth of contaminating microorganisms. The feedstock may include a sugar-containing material (e.g., carbon source), a nitrogen-containing material (e.g., nitrogen source), or trace vitamins and minerals. The feedstock may be provided to the reactor in a single influent stream or may be divided into multiple influent streams. The sugar-containing material and the nitrogen-containing material may be provided to the reactor in a single influent stream. Alternately, or in addition to, the sugar-containing material and nitrogen-containing material may be provided to the reactor in different influent streams.

The influent streams may have the same volumetric flow rate or different volumetric flow rates. The ratio of total influent volumetric flow rate (volume/time) to the reactor volume (volume) may be greater than or equal to about 0.05 inverse time ($t^{-1}$), 0.1 $t^{-1}$, 0.2 $t^{-1}$, 0.3 $t^{-1}$, 0.4 $t^{-1}$, 0.5 $t^{-1}$, or greater. The ratio of total influent volumetric flow rate to the reactor volume may be less than or equal to about 0.5 $t^{-1}$, 0.4 $t^{-1}$, 0.3 $t^{-1}$, 0.2 $t^{-1}$, 0.1 $t^{-1}$, 0.05 $t^{-1}$, or less. The influent volumetric flow rates may be constant or may be modulated. The influent rate may be operated to maintain a dilution rate in the reactor. The dilution rate, which may be the ratio of the total flow rate (volume/time) to the culture volume (volume), may be greater than or equal to about 0.05 $t^{-1}$, 0.1 $t^{-1}$, 0.2 $t^{-1}$, 0.3 $t^{-1}$, 0.4 $t^{-1}$, 0.5 $t^{-1}$, 0.6 $t^{-1}$, 0.7 $t^{-1}$, or greater. The dilution rate may be less than or equal to about 0.7 $t^{-1}$, 0.6 $t^{-1}$, 0.5 $t^{-1}$, 0.4 $t^{-1}$, 0.3 $t^{-1}$, 0.2 $t^{-1}$, 0.1 $t^{-1}$, 0.05 $t^{-1}$, or less. The influent flow rate(s) may be modulated as a function of operating conditions. Operating conditions that may be monitored and used to modulate influent flow rate(s) may include pH, pressure, conductivity, temperature, dissolved oxygen, optical density, acoustic density, gas analysis (e.g., $CO_2$), liquid volume, and/or stir speed. For example, the flow rate of the acidic material or basic material may be modulated based on the difference between the set point of the pH in the reactor and the actual measured pH value in the reactor. Similarly, the influent flow rate of the feedstock may be modulated based on the measured values of the pH, dissolved oxygen, optical density (OD) of the effluent, acoustic density of the effluent, or any other measured parameter. The operating parameters of the reactor may be measured at one or more locations internal to the reactor. Alternatively, or in addition to, the operating parameters may be measured in one or more of the influent streams, effluent streams, or recycle streams of the reactor. Cell growth may be monitored by measuring the cell density in the reactor, effluent streams, or both the reactor and effluent streams. Cell density may be monitored continuously or at specific time intervals. This may include measuring cell density at least once every at least 30 seconds, 1 minute, 2 minutes, 5 minutes, 10 minutes, 15 minutes, 20 minutes, 30 minutes, 45 minutes, 1 hour, 2 hours, or more. Cell density may be measured by optical density techniques, acoustic density techniques, acoustic spectroscopy techniques, or any other cell density measurement technique.

The volumetric flow rate of the influent may include the volumetric flow rates of the acidic material, the basic material, the sugar-containing material, the nitrogen-containing material, and/or trace vitamins and minerals. The acid material may comprise an aqueous acid such as hydrochloric acid, phosphoric acid, acetic acid, or any other acid compatible with unicellular growth. The basic material may comprise an aqueous base such as sodium hydroxide, potassium hydroxide, calcium hydroxide, or any other base compatible with unicellular growth. The trace minerals may include, but are not limited to, copper, zinc, iron, iodine, magnesium, manganese, calcium, sodium, cobalt, boron, molybdenum, and/or potassium.

The sugar-containing carbon source material in the feedstock may include one or more of sugar, soft agricultural waste, or hard agricultural waste. The carbon source may not be a sugar-containing carbon source. For example, the carbon source may be a polyol such as glycerol, erythritol, starch hydrolysates, isomalt, lactitol, maltitol, mannitol, sorbitol, or xylitol. In an example, the polyol is glycerol. The sugar may include one or more of a refined sugar, a purified sugar, or a crude sugar. The predominant component of the sugar-containing carbon source material may be a sugar or an agricultural waste. The agricultural waste may be broken down to a sugar by enzymatic treatment, chemical treatment, heat treatment, or digestion by a microorganism. The soft or hard agricultural waste may be supplemented with a sugar. Alternatively, or in addition to, the soft or hard agricultural waste may not be supplemented with a sugar. The sugar-containing material may comprise less than or equal to about 75%, 50%, 40%, 30%, 20%, 15%, 10%, 5%, 4%, 3%, 2%, 1%, or less of purified, refined, or crude sugar on a dry matter basis. Alternatively, the sugar-containing material may not contain a refined, purified, or crude sugar.

The sugar-containing material may comprise at least a portion of soft or hard agricultural waste. Soft agricultural waste may refer to agricultural waste with a low lignin content (e.g., less than 10% by dry weight). Soft agricultural waste may include fruit and vegetable wastes, such as wastes from actinidiaceae crops, amaryllidaceae crops, anacardiaceae crops, annonaceae crops, apiaceae crops, asteraceae crops, boraginaceae crops, brassicaceae crops, bromeliaceae crops, chenopodiaceae crops, compositae crops, convolvulaceae crops, cucurbitaceae crops, ebenaceae crops, ericaceae crops, fabaceae crops, grossulariaceae crops, lamiaceae crops, lauraceae crops, leguminosae crops, lythraceae crops, malvaceae crops, moraceae crops, myrthaceae crops, oleaceae crops, passifloraceae crops, poaceae crops, polygonaceae crops, rosaceae crops, rutaceae crops, sapindaceae crops, solanaceae crops, verbenaceae crops, vitaceae crops, aingiberaceae crops, or any other large seasonal crop. Soft agricultural waste may also contain protein from animal products such as whey, butter, whole or partial milk, blood, extracts of tissues, muscle, or whole animals. Hard agricultural wastes may include grains, grasses, and non-fruit and vegetable biomass such as corn stover, rice hulls, and/or grain stalks. Hard agricultural waste may also include yard and landscape wastes. Hard agricultural waste may have a higher lignin content (e.g., greater than 25% by dry weight) than soft agricultural waste. The sugar-containing material may be a mixture of both soft and hard agricultural waste. Alternatively, or in addition to, the sugar-containing material may be either soft or hard agricultural waste. The lignin content of the sugar-containing material may be less than or equal to about 40%, 30%, 25%, 20%, 15%, 10%, 5%, 4%, 3%, 2%, 1%, or less. In one example, the sugar-containing material may contain zero percent lignin. The sugar-containing material may be pretreated to remove lignin and other solid components prior to addition to the reactor. Pretreatment may include, but is not limited to, steam explosion, acid treatment, base treatment, grinding, milling, pasteurization, centrifugation, filtration, and/or homogenization.

The unicellular organism may be selected or engineered for the organism's ability to uptake and convert agricultural waste to biomass. Sporulation efficiency may be used to monitor and select unicellular organisms with the ability to uptake and convert agricultural waste to biomass. Selection or engineering of the unicellular organism may include directed evolution or metabolic engineering. Unicellular organisms may be selected for their ability to produce biomass at a high growth rate from an agricultural waste feedstock or a feedstock containing both agricultural waste and a supplemental sugar. The doubling time of the unicellular organism grown on an agricultural waste feedstock may be less than or equal to about 4 hours, 3 hours, 2 hours, 1.5 hours, 1 hour, 30 minutes, 10 minutes, 5 minutes, 1 minute, or less. The doubling time of a unicellular organism grown on an agricultural waste feedstock supplemented with a sugar source may be less than or equal to about 5 hours, 4 hours, 3 hours, 2 hours, 1.5 hours, 1 hour, 30 minutes, 15 minutes, 10 minutes, 5 minutes, 1 minute, or less.

The unicellular organism may be grown in a liquid culture, solid culture, or solid support culture. Unicellular organisms grown in a liquid culture may be suspended in the liquid during growth. A liquid culture may not have a solid support media and unicellular organisms grown in a liquid culture may be grown in the absence of the solid support media. Unicellular organisms grown in a solid support culture may be grown in a liquid media with the aid of a support media. The support media may be inert (e.g., not consumed by the unicellular organism) or may comprise a starch that is consumed by the organism. The unicellular organism may form a layer and grown on the support media. Unicellular organisms grown on a solid culture may be grown in the absence of a liquid media. The solid culture may include the nutrients to support growth (e.g., carbon and nitrogen sources). In an example, the unicellular organism is fungi or bacteria and is grown in a liquid culture in the absence of a support media. The unicellular organism may be selected for the ability to grow in the absence of a support media.

The nitrogen-containing material (e.g., nitrogen source) may comprise nitrate salts, ammonia salts, urea, pre-digested polypeptides, peptones, hydrolysates (e.g., soy hydrolysate), nitrogen gas, ammonium hydroxide, or any combination thereof. Nitrate salts may include, but are not limited to, potassium nitrate, ammonium nitrate, sodium nitrate, or calcium nitrate. Ammonia salts may include, but are not limited to, ammonium sulfate, ammonium nitrate, ammonium carbonate, or ammonium chloride. Alternatively, or in addition to, the nitrogen-containing material may comprise other sources of nitrogen such as a bulk proteins (e.g., soy meal or whey from animal milk) or pre-digested polypeptides (e.g., peptone, tryptone, or yeast extract). Alternatively, or in addition to, the nitrogen-containing material may comprise simple nitrogen-carbon compounds such as urea. The nitrogen-containing material may comprise a combination of salts and bulk proteins or pre-digested polypeptides derived from agricultural waste. The nitrogen-containing material may comprise greater than or equal to about 10%, 20%, 30%, 40%, 50%, 60%, 70%, 80%, 90%, or more nitrate salts, ammonia salts, or urea compounds. The nitrogen-containing material may comprise less than or equal to about 90%, 80%, 70%, 60%, 50%, 40%, 30%, 30%, 10%, or less nitrate salts, ammonia salts, or urea compounds. The nitrogen-containing material may comprise from about 10% to 20%, 10% to 30%, 10% to 40%, 10% to 50%, 10% to 60%, 10% to 70%, 10% to 80%, or 10% to 90%.

The unicellular organism may be selected or engineered for the organism's ability to uptake and convert nitrate salts, ammonia salts, or urea to biomass. Sporulation efficiency may be used to monitor and select unicellular organisms with the ability to uptake and convert nitrate salts, ammonia salts, or urea to biomass. Selection or engineering of the unicellular organism may include directed evolution or metabolic engineering. Unicellular organisms may be selected for their ability to produce biomass at a high growth rate from nitrate salts, ammonia salts, urea feedstock, or any combination thereof, with or without a supplemental nitrogen source. The doubling time of the unicellular organism grown on a nitrate salt, ammonia salt, or urea compound feedstock may be less than or equal to about 10 hours, 8 hours, 6 hours, 4 hours, 3 hours, 2 hours, 1.5 hours, 1 hour, 30 minutes, 15 minutes, 10 minutes, 5 minutes, 1 minute, or less. The doubling time of a unicellular organism grown on a nitrate salt, ammonia salt, or urea compound feedstock supplemented with a nitrogen source may be less than or equal to about 10 hours, 8 hours, 6 hours, 4 hours, 2 hours, 1.5 hours, 1 hour, 30 minutes, 15 minutes, 10 minutes, 5 minutes, 1 minute, or less.

The reactor may have one or more effluent streams. The effluent stream may include a single stream or multiple streams (e.g., 2, 3, 4, 5, or more streams). Alternatively, or in addition to, the effluent stream may be a single stream that is split into multiple streams. The flow rate of the effluent stream may be less than, greater than, or equal to the flow rate of the influent stream. The flowrate of the effluent stream may be set to maintain the fluid volume of the reactor. The volumetric flow rate of the effluent stream may be equal to the volumetric flow rate of the influent streams plus the increase in volume within the reactor due to increase of biomass (e.g., reproduction of unicellular organisms). The ratio of total effluent volumetric flow rate (volume/time) to the reactor volume (volume) may be greater than or equal to about $0.05\ t^{-1}$, $0.1\ t^{-1}$, $0.2\ t^{-1}$, $0.3\ t^{-1}$, $0.4\ t^{-1}$, $0.5\ t^{-1}$, or greater. The ratio of the total volumetric effluent flow rate to the reactor volume may be less than or equal to about $0.5\ t^{-1}$, $0.4\ t^{-1}$, $0.3\ t^{-1}$, $0.2\ t^{-1}$, $0.1\ t^{-1}$, $0.05\ t^{-1}$, or less. The ratio of total effluent volumetric flow rate to the reactor volume may be from about $0.05\ t^{-1}$ to $0.1\ t^{-1}$, $0.05\ t^{-1}$ to $0.2\ t^{-1}$, $0.05\ t^{-1}$ to $0.3\ t^{-1}$, $0.05\ t^{-1}$ to $0.4\ t^{-1}$, or $0.05\ t^{-1}$ to $0.5\ t^{-1}$. The flow rate of the effluent stream may be independently controlled (e.g., with a valve or flow meter) or the effluent stream may be dependent upon the influent flow rate (e.g., overflow through a side port).

The effluent stream may be separated into a solid phase and a liquid phase. The effluent stream may be separated by centrifugation, filtration, settling, vacuum filtration, or any other method for separating a solid and liquid phase. The solids phase may predominantly contain unicellular organisms and non-consumed solid feedstock. The solid phase may contain less than or equal to about 70%, 60%, 50%, 40%, 30%, 20%, 10%, or less water by mass. The liquid phase may predominantly contain liquid media. The liquid phase may contain less than or equal to about 30%, 25%, 20%, 15%, 10%, 5%, or less unicellular organisms by mass. A portion, or all, of the liquid media may be recycled to one or more of the influent streams. The recycle ratio (e.g., the mass flow of the recycle stream divided by the mass flow of the influent stream) may be greater than or equal to about 0.05, 0.1, 0.2, 0.3, 0.4, 0.5, or greater. The recycle ratio may be from about 0.05 to 0.2, 0.1 to 0.3, 0.2 to 0.4, 0.3 to 0.5, 0.4 to 0.6, or 0.5 to 0.7.

The solid phase may be a unicellular organism-containing product (e.g., fungus-containing product, bacteria-containing product, algae-containing product, or an animal cell-containing product). The unicellular organism-containing product may be added to a food product. The food product may be suitable for human or animal consumption. The animal may be livestock or a companion animal. Livestock may include cattle, swine, sheep, goats, poultry, llama, or any other farmed livestock. Companion animals may include dogs, cats, rodents, rabbits, horses, birds, or any other companion animal. The solid phase of the effluent may comprise whole cells. The whole cells may be a whole cell product (e.g., fungus-, bacteria-, algae- or animal cell-containing product). The whole cell product may be added to a food product without further purification of the whole cell product. The whole cells may be unprocessed such that the cell wall is intact or may be processed to lyse the cells. The whole cell product may contain all portions of the cell, including the cell membrane, cytoplasm, cell wall, and nucleus of a cell. Alternatively, or in addition to, the whole cell product may be purified to remove non-cell biomass, such as the feedstock and residual liquids. The whole cell product may contain greater than or equal to about 40%, 50%, 60%, 70%, 80%, 90%, or more whole cells by weight. The whole cell product may contain from about 40% to 60%, 40% to 70%, 40% to 80%, or 40% to 90% whole cells. The whole cell product may make up greater than or equal to about 20%, 30%, 40%, 50%, 60%, 70%, 80%, 90%, or more of the food product on a dry matter basis. The whole cell product may make up from about 20% to 40%, 20% to 50%, 20% to 60%, 20% to 70%, 20% to 80%, or 20% to 90% of the food product on a dry matter basis. In an example, the whole cell product is a fungus-containing product and the fungus-containing product makes up greater than 30% of the food product by dry weight. In an example, the whole cell product is a fungus-containing product and the fungus-containing product makes up greater than 40% of the food product by dry weight. In an example, the whole cell product is a fungus-containing product and the fungus-containing product makes up greater than 50% of the food product by dry weight. In an example, the whole cell product is a fungus-containing product and the fungus-containing product makes up greater than 60% of the food product by dry weight.

The solid phase may be purified to form a protein concentrate. The protein concentrate may be the unicellular organism-containing product (e.g., fungus-, bacteria-, algae- or animal cell-containing product). The protein within the whole cells may be extracted from the cells and further purified. The proteins may be isolated by cell lysis and protein extraction. Cell lysis and protein extraction may be performed by a single technique or may be performed by multiple techniques. For example, cell lysis may include mechanical, chemical, and/or enzymatic lysis techniques. Lysis techniques may include, but are not limited to, pressure gradient lysis, manual grinding, sonication, liquid homogenization, freeze-thaw, thermal lysis, osmotic lysis, enzymatic lysis, and/or treatment with organic solvents, surfactants, chelating agents, acid, base, detergents, and/or chaotropic agents. The proteins may be extracted simultaneously with cell lysis using one or more of the aforementioned methods. Alternatively, or in addition to, protein extraction may be performed after cell lysis. Methods for separating the protein from the non-protein components of the lysed cells include, but are not limited to, salt extraction, alcohol extraction, acid or base extraction, affinity chromatography, size exclusion chromatography, liquid-liquid extraction, acetone precipitation, tangential flow filtration, dialysis, and other filtration techniques. Proteins may be purified using one or more of the aforementioned techniques. The extracted protein may be denatured by heat, alcohol, acid, base, or salt and washed with a neutral, acidic, or basic water to further remove non-protein components. The extracted protein may be a protein concentrate. The protein concentrate may contain greater than or equal to about 40%, 50%, 60%, 70%, 80%, or more protein on a dry matter basis. The protein concentrate may contain from about 40% to 50%, 40% to 60%, 40% to 70%, 40% to 90%, or 40% to 90% protein on a dry matter basis. In an example, the protein concentrate comprises from 60% to 90% protein by dry weight. The protein concentrate may be further purified to remove excess nucleic acid molecules. The protein concentrate may be added to a food product for human or animal consumption. The protein concentrate may make up greater than or equal to about 20%, 30%, 40%, 50%, 60%, 70%, 80%, 90%, or more of the food product on a dry matter basis. The protein concentrate may make up from about 20% to 40%, 20% to 50%, 20% to 60%, 20% to 70%, 20% to 80%, or 20% to 90% of the food product on a dry matter basis. In an example, the protein concentrate is a fungal protein concentrate and the fungal protein concentrate makes up greater than or equal to 30% of the food product by dry weight. In an example, the protein concentrate is a fungal protein concentrate and the fungal protein concentrate makes up greater than or equal to 40% of the food product by dry weight. In an example, the protein concentrate is a fungal protein concentrate and the fungal protein concentrate makes up greater than or equal to 50% of the food product by dry weight. In an example, the protein concentrate is a fungal protein concentrate and the fungal protein concentrate makes up greater than or equal to 60% of the food product by dry weight.

The solid phase may be further purified to form a protein isolate. The protein within the whole cells may be extracted from the cells and further purified. Cell lysis and protein extraction may be performed by a single technique or may be performed by multiple techniques. For example, cell lysis may include mechanical, chemical, and/or enzymatic lysis techniques. Lysis techniques may include, but are not limited to, pressure gradient lysis, manual grinding, sonication, liquid homogenization, freeze-thaw, thermal lysis, osmotic lysis, enzymatic lysis, and/or treatment with organic solvents, surfactants, chelating agents, acid, base, detergents, and/or chaotropic agents. The proteins may be extracted simultaneously with cell lysis using one or more of the aforementioned methods. Alternatively, or in addition to, protein extraction may be performed after cell lysis. Methods for separating the protein from the non-protein components of the lysed cells include, but are not limited to, salt extraction, alcohol extraction, acid or base extraction, affinity chromatography, size exclusion chromatography, liquid-liquid extraction, acetone precipitation, tangential flow filtration, dialysis, and/or other filtration techniques. Proteins may be purified using one or more of the aforementioned techniques. The extracted protein may be denatured by heat, alcohol, acid, base, or salt and washed with a neutral, acidic, or basic water to further remove non-protein components. Protein purification methods may be used until a desired purity is achieved. The protein isolate may contain greater than or equal to about 80%, 85%, 90%, 95%, 98%, or more protein on a dry matter basis. The protein isolate may contain from about 80% to 85%, 80% to 90%, 80% to 95%, or 80% to 98% protein on a dry matter basis. The protein isolate may be further purified to remove excess nucleic acid molecules. The protein isolate may be added to a food product. The protein isolate may make up greater than or equal to about 20%, 30%, 40%, 50%, 60%, 70%, 80%, 90%, or more of the food product on a dry matter basis. The protein isolate may make up from about 20% to 40%, 20% to 50%, 20% to 60%, 20% to 70%, 20% to 80%, or 20% to 90% of the food product on a dry matter basis. In an example, the protein isolate is a fungal protein isolate and the fungal protein isolate makes up greater than or equal to 30% of the food product by dry weight. In an example, the protein isolate is a fungal protein isolate and the fungal protein isolate makes up greater than or equal to 40% of the food product by dry weight. In an example, the protein isolate is a fungal protein isolate and the fungal protein isolate makes up greater than or equal to 50% of the food product by dry weight. In an example, the protein isolate is a fungal protein isolate and the fungal protein isolate makes up greater than or equal to 60% of the food product by dry weight.

The unicellular organism-containing product (e.g., whole cell, protein concentrate, or protein isolate) may or may not be treated to remove nucleic acid molecules (e.g., ribonucleic acid (RNA) or deoxyribonucleic acid (DNA)). Nucleic acid molecules in the food product may alter the taste of the food product. For example, RNA may degrade and impart an umami-like flavor to the food product. The amount of nucleic acid molecules in the unicellular organism-containing product may be removed by heat degradation (e.g., at temperatures below 100° C.), enzyme treatment, or purification. The native (e.g., without removal) amount of RNA in the unicellular organism-containing product may be greater than or equal to about 2%, 3%, 4%, 5%, 6%, 7%, 8%, 9%, 10%, 15%, 20%, or more on a dry matter basis. In an example, the unicellular organism-containing product may contain greater than about 4% RNA on a dry matter basis. In an example, the unicellular organism-containing product may contain greater than about 6% RNA on a dry matter basis. In an example, the unicellular organism-containing product may contain greater than about 8% RNA on a dry matter basis. In an example, not removing or reducing the concentration of nucleic acid molecules (e.g., RNA and DNA) give the food product a more umami or cooked meat or broth flavor of the food product. In an example, the unicellular organism-containing product is processed or treated to remove nucleic acids (e.g., RNA and/or DNA). The unicellular organism-containing product may be processed to reduce the concentration of nucleic acids to less than or equal to about 4% 3%, 2%, 1%, 0.5%, 0.1%, or less by dry weight. The unicellular organism-containing product may be processed to reduce the concentration of RNA to less than or equal to about 4% 3%, 2%, 1%, 0.5%, 0.1%, or less by dry weight. In an example, the unicellular organism-containing product may contain less than about 4% RNA on a dry matter basis. In an example, the unicellular organism-containing product may contain less than 6% RNA on a dry matter basis. In an example, the unicellular organism-containing product may contain less than 8% RNA on a dry matter basis. In an example, removing or reducing the concentration of nucleic acid molecules (e.g., RNA and DNA) reduces an amount of umami or cooked meat or broth flavor of the food product.

The food product may be produced by combining a unicellular organism-containing product with one or more other ingredients. The one or more other ingredients may include flour, oil, flavoring agents, preservatives, nutritional supplements, dyes, or other edible materials. The food product may contain animal products or may not contain animal products. Animal products may include blood, milk, eggs, connective tissue, fats, oils, proteins, and/or other materials derived from an animal. In an example, the food product does not contain animal proteins. In an example, the food product does not contain an animal protein, but does contain an animal oil (e.g., fish oil). In an example, the food product does not contain any animal materials or products. In an example, a food product for human, animal, or companion animal consumption comprises whole animal cells, protein concentrate derived from animal cells, protein isolate derived from animal cells, or any combination thereof. The animal cells may be synthetically cultured outside of an animal. The food product may comprise greater than or equal to about 10%, 20%, 30%, 40%, 50%, 60%, 70%, 80%, 90%, or more of whole animal cells. The food product may comprise less than or equal to about 90%, 80%, 70%, 60%, 50%, 40%, 30%, 30%, 10%, or less of whole animal cells. The food product may comprise from about 10% to 20%, 10% to 30%, 10% to 40%, 10% to 50%, 10% to 60%, 10% to 70%, 10% to 80%, or 10% to 90% of whole animal cells. In an example, the food product contains no whole animal cells.

The unicellular organism-containing product may contain whole cells or purified proteins. The unicellular organism-containing product may contain a single type of unicellular organism or protein from a single unicellular organism or may contain multiple different types of unicellular organisms or proteins from the multiple different types of unicellular organisms. The unicellular organism-containing product may comprise a mixture of types of fungi, bacteria, algae, animal cells, or any combination thereof. In an example, the unicellular organism-containing product is a fungus-containing product and the fungus-containing product comprises one or more different types of fungus. In an example, the fungus-containing product includes *Aspergillus oryzae* and *Saccharomyces cerevisiae*. The *Aspergillus oryzae* and *Saccharomyces cerevisiae* may be present in the fungus-containing product at a ratio of greater than or equal to about 1:1, 1:2, 1:3, 1:4, 1:5, 1:6, 1:7, 1:8, 1:9, 1:10, or more. The *Aspergillus oryzae* and *Saccharomyces cerevisiae* may be present in the fungus-containing product at a ratio of less than or equal to about 1:10, 1:9, 1:8, 1:7, 1:6, 1:5, 1:4, 1:3, 1:2, 1:1, or less. The *Aspergillus oryzae* and *Saccharomyces cerevisiae* may be present in the fungus-containing product at a ratio from about 1:1 to 1:2, 1:1 to 1:3, 1:1 to 1:4, 1:1 to 1:5, 1:1 to 1:6, 1:1 to 1:7, 1:1 to 1:8, 1:1 to 1:9, 1:1 to 1:10, 1:10 to 1:9, 1:10 to 1:8, 1:10 to 1:7, 1:10 to 1:6, 1:10 to 1:5, 1:10 to 1:4, 1:10 to 1:3, 1:10 to 1:2, or 1:10 to 1:1. In an example, *Aspergillus oryzae* and *Saccharomyces cerevisiae* are present at a ratio from about 1:5 to 1:2.

The unicellular organism-containing product may be mixed with other ingredients to form a homogenous or semi-homogenous food product. The unicellular organism-containing product added to or mixed with other ingredients may be a dry unicellular organism-containing product (e.g., having a water content of less than 15%, 10%, 5%, 1%, or less) or a wet biomass (e.g., having a water content of at least 15%, 30%, 40%, 50%, or more). The wet biomass may be processed into a dry unicellular organism-containing product by lyophilization, heating, or vacuum drying. The wet biomass may be heated at a temperature of greater than or equal to about 30° C., 40° C., 50° C., 60° C., 70° C., 80° C., 90° C., 100° C., or more to generate a dry unicellular organism-containing product. The wet biomass may be dried for greater than or equal to 1 minute, 2 minutes, 3 minutes, 4 minutes, 5 minutes, 6 minutes, 8 minutes, 10 minutes, 12 minutes, 15 minutes, 20 minutes, 30 minutes, 40 minutes, 50 minutes, 60 minutes, 90 minutes, 120 minutes, 150 minutes, 180 minutes, 240 minutes, 300 minutes, 400 minutes, 500 minutes, 600 minutes, or more to dry generate the dry unicellular organism-containing product. The wet biomass may be dried from 1 minute to 2 minutes, 1 minute to 3 minutes, 1 minute to 4 minutes, 1 minute to 5 minutes, 1 minute to 6 minutes, 1 minute to 8 minutes, 1 minute to 10 minutes, 1 minute to 12 minutes, 1 minute to 15 minutes, 1 minute to 20 minutes, 1 minute to 30 minutes, 1 minute to 40 minutes, 1 minute to 50 minutes, 1 minute to 60 minutes, 1 minute to 90 minutes, 1 minute to 120 minutes, 1 minute to 150 minutes, 1 minute to 180 minutes, 1 minute to 240 minutes, 1 minute to 300 minutes, 1 minute to 400 minutes, 1 minute to 500 minutes, 1 minute to 600 minutes. In an example, the wet biomass is *Aspergillus oryzae* and the wet biomass is dried at a temperature of greater than or equal to 80° C. from about 180 minutes to 240 minutes. In an example, the wet biomass is *Aspergillus oryzae* and the wet biomass is dried at a temperature of greater than or equal to 60° C. from about 360 minutes to 480 minutes. Drying the wet biomass may cause caramelization of the unicellular organism-containing product through the Maillard reaction. Drying the wet biomass may alter the flavor of the unicellular organism-containing product and food product by increasing the umami notes in the product. In an example, the food product may be produced by combining dry unicellular organism-containing product with other ingredients.

The unicellular organism-containing product may be mixed or combined with one or more ingredients to generate the food product. The one or more ingredients may be wet ingredients or dry ingredients. The unicellular organism-containing product may be mixed with other ingredients until well combined (e.g., the mixture is substantially homogenous or semi-homogenous). Mixing may be performed for greater than or equal to about 1 minute, 2 minutes, 3 minutes, 4 minutes, 5 minutes, 6 minutes, 8 minutes, 10 minutes, 12 minutes, 15 minutes, 20 minutes, 30 minutes, 40 minutes, 50 minutes, 60 minutes, 90 minutes, 120 minutes, or more minutes. Mixing may be from about 1 minute to 2 minutes, 1 minute to 3 minutes, 1 minute to 4 minutes, 1 minute to 5 minutes, 1 minute to 6 minutes, 1 minute to 8 minutes, 1 minute to 10 minutes, 1 minute to 12 minutes, 1 minute to 15 minutes, 1 minute to 20 minutes, 1 minute to 30 minutes, 1 minute to 40 minutes, 1 minute to 50 minutes, 1 minute to 60 minutes, 1 minute to 90 minutes, or 1 minute to 120 minutes. In an example, the unicellular organism-containing product and other ingredients are mixed from about 5 minutes to 15 minutes.

The unicellular organism-containing product may be a wet ingredient or a dry ingredient. The food product may comprise greater than or equal to about 3%, 4%, 6%, 8%, 10%, 15%, 20%, 25%, 30%, 40%, 50%, 60%, 70%, 80%, 90%, or more unicellular organism-containing product by wet weight. The food product may comprise less than or equal to about 90%, 80%, 70%, 60%, 50%, 40%, 30%, 25%, 20%, 15%, 10%, 8%, 6%, 4%, 3%, or less unicellular organism-containing product by wet weight. The food product may comprise from about 3% to 4%, 3% to 6%, 3% to 8%, 3% to 10%, 3% to 15%, 3% to 20%, 3% to 25%, 3% to 30%, 3% to 40%, 3% to 50%, 3% to 60%, 3% to 70%, 3% to 80%, or 3% to 90%. In an example, the unicellular organism-containing product is a fungus-containing product and the food product contains at least 3% fungus-containing product by wet weight. In an example, the fungus-containing product is made up of *Aspergillus oryzae* and the food product comprises at least 3% *Aspergillus oryzae* by wet weight. In another example, the fungus-containing product is made up of *Aspergillus oryzae* and the food product comprises from 3% to 70% by wet weight. In another example, the fungus-containing product is made up of *Aspergillus oryzae* and *Saccharomyces cerevisiae* and the food product comprises at least 3% *Aspergillus oryzae*. In another example, the fungus-containing product is made up of *Aspergillus oryzae* and *Saccharomyces cerevisiae* and the food product comprises at least 6% *Aspergillus oryzae*. In another example, the fungus-containing product is made up of *Aspergillus oryzae* and *Saccharomyces cerevisiae* and the food product comprises at least 8% *Aspergillus oryzae*. In another example, the fungus-containing product is made up of *Aspergillus oryzae* and *Saccharomyces cerevisiae* and the food product comprises at least 10% *Aspergillus oryzae*.

In another example, the food product may be produced by combining wet unicellular organism-containing product with other ingredients to form a dough or mixture. The dough or mixture may be incubated to allow for fermentation of the dough or mixture. Fermentation may have a leavening effect on the food product. The dough or mixture may be incubated at ambient temperature (e.g., approximately 18° C. to 25° C.). Alternatively, or in addition to, the dough or mixture may be incubated at a temperature of greater than or equal to about 20° C., 25° C., 30° C., 35° C., 40° C., 45° C., or more. The dough or mixture may be incubated at a temperature from about 20° C. to 25° C., 20° C. to 30° C., 20° C. to 35° C., 20° C. to 40° C., or 20° C. to 45° C. The dough or mixture may be incubated for greater than or equal to about 1 minute, 2 minutes, 3 minutes, 4 minutes, 5 minutes, 6 minutes, 8 minutes, 10 minutes, 15 minutes, 20 minutes, 25 minutes, 30 minutes, 40 minutes, 50 minutes, 60 minutes, 75 minutes, 90 minutes, 120 minutes, 150 minutes, 180 minutes, 210 minutes, 240 minutes, 270 minutes, 300 minutes, 400 minutes, 500 minutes, or more to ferment the dough or mixture. The dough or mixture may be incubated for less than or equal to about 500 minute, 400 minutes, 300 minutes, 270 minutes, 240 minutes, 210 minutes, 180 minutes, 150 minutes, 120 minutes, 90 minutes, 75 minutes, 60 minutes, 50 minutes, 40 minutes, 30 minutes, 25 minutes, 20 minutes, 15 minutes, 10 minutes, 8 minutes, 6 minutes, 5 minutes, 4 minutes, 3 minutes, 2 minutes, 1 minute, or less to ferment the dough or mixture. The dough or mixture may be incubated from about 1 minute to 2 minutes, 1 minute to 3 minutes, 1 minute to 4 minutes, 1 minute to 5 minutes, 1 minute to 6 minutes, 1 minute to 8 minutes, 1 minute to 10 minutes, 1 minute to 15 minutes, 1 minute to 20 minutes, 1 minute to 25 minutes, 1 minute to 30 minutes, 1 minute to 40 minutes, 1 minute to 50 minutes, 1 minute to 60 minutes, 1 minute to 75 minutes, 1 minute to 90 minutes, 1 minute to 120 minutes, 1 minute to 150 minutes, 1 minute to 180 minutes, 1 minute to 210 minutes, 1 minute to 240 minutes, 1 minute to 270 minutes, 1 minute to 300 minutes, 1 minute to 400 minutes, 1 minute to 500 minutes, or more to ferment the dough or mixture. In an example, the dough or mixture is incubated at ambient temperature from about 30 minutes to 60 minutes.

Alternatively, or in addition to, the unicellular organism-containing product is added to the other ingredients as a sprayed on layer or coating on an external surface of the food product. In an example, the unicellular organism-containing product (e.g., fungus-containing product) is mixed with other ingredients to form a homogenous or semi-homogenous food product and is not a spray or coating on an outer surface of the food product.

The unicellular organism-containing product may be mixed or combined with one or more flours (e.g., plant-derived flours) to generate the food product. The flours may be derived from grain products. The food product may contain less than or equal to about 70%, 60%, 50%, 40%, 30%, 20%, 10%, 5%, or less flour on a dry matter basis. The food product may contain from about 20% to 30%, 20% to 40%, 20% to 50%, 20% to 60%, or 20% to 70% flour on a dry matter basis. The food product may contain a single type of flour or multiple types of flour. The flour may include, but is not limited to, wheat flour, flaxseed flour, rice flour, corn flour, corn gluten, corn bran, corn starch, barley flour, sorghum flour, oat flour, potato flour, rye flour, soybean flour, or any combinations thereof. In an example, the flour is wheat all-purpose flour, flaxseed flour, oat flour, buckwheat flour (e.g., whole grain buckwheat flour), or brown rice flour. In an example, the food product contains from 5% to 50% flour by dry weight.

The unicellular organism-containing product may be mixed or combined with one or more meals, powders, purees, starches or other additional ingredients to generate the food product. The meals, powders, purees, or starches may be derived from any grain products, fruit products, legumes, and/or vegetable products. The food product may contain less than or equal to about 70%, 65%, 60%, 55%, 50%, 45%, 40%, 35%, 30%, 25%, 20%, 15%, 10%, 9%, 8%, 7%, 6%, 5%, 4%, 3%, 2%, 1%, 0.5% or less weight percent of a given meal, powder, puree, starch or other additional ingredient, and in some cases, on a dry matter basis. The food product may contain greater than or equal to about 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70% or more weight percent of a given meal, powder, puree, starch or other additional ingredient, and in some cases, on a dry matter basis. The food product may contain from about 0.2% to 0.8%, 0.2% to 1%, 0.5% to 1.3%, 0.5% to 1.5%, 0.5% to 1.6%, 0.5% to 3%, 2% to 8%, 3% to 8%, 4% to 12%, 5% to 8%, 10% to 15%, 10% to 25%, 10% to 30%, 15% to 30%, 18% to 25%, 20% to 30%, 20% to 40%, 20% to 50%, 20% to 60%, 20% to 70%, 25% to 35%, 30% to 50%, 45% to 65% weight percent of a given meal, powder, puree, or starch or other additional ingredient, and in some cases, on a dry matter basis. The food product may contain a single type of meal, powder, puree, starch or other additional ingredient or multiple types of meals, powders, purees, starches, or other additional agreements. Non-limiting examples of powders, purees, starches or other additional ingredients include, salt, baking soda, antioxidants, preservatives, potassium chloride, amino acids, an oil (including one or more described elsewhere herein), disodium phosphate, mineral mixes premixes, modified or unmodified potato starch, pumpkin or squash puree, flax seed meal, flaxseed, nut butters (e.g., peanut or almond butter), carrot powder, potato flour (e.g., sweet potato flour), potato powder (e.g., sweet potato powder), rice flour, oat flour, peas (e.g., pea protein, ground peas), fruits (including dried fruits, with non-limiting examples of fruits including apples, oranges, pears, peaches, nectarines, tangerines, blueberries, raspberries, strawberries, blackberries, cherries, watermelon, plums, cantaloupe, bananas), dried potatoes, dried chickpeas, chickpea flour, yeast (e.g., dried yeast), ground peas, natural flavors, vitamins, protein powders (e.g., pumpkin protein powders) or any combination thereof. Moreover, balances of food product preparations can be made with a liquid medium, such as water.

The unicellular organism-containing product may be mixed or combined with one or more plant-derived and non-plant derived oils to generate the food product. The food product may contain less than or equal to about 40%, 35%, 30%, 25%, 20%, 15%, 14%, 13%, 12%, 11%, 10%, 9%, 8%, 7%, 6%, 5%, 4%, 3%, 2%, 1%, 0.5%, or less weight percent oil, and in some cases, on a dry matter basis. The food product may contain greater than or equal to about 0.5%, 1%, 2%, 3%, 4%, 5%, 6%, 7%, 8%, 9%, 10%, 11%, 12%, 13%, 14%, 15%, 20%, 25%, 30%, 35%, 40% or more weight percent oil, and in some cases, on a dry matter basis. The food product may contain from about 0.1% to 0.5%, 0.5% to 1%, 0.1% to 1%, 1% to 2%, 1% to 3%, 1% to 4%, 1% to 5%, 1% to 10%, 1% to 20%, 1% to 30%, or 1% to 40%, 4%-8%, 4%-12%, 5%-10% 10%-15%. 20% to 25%, 20% to 30%, weight percent oil, and in some cases, on a dry matter basis. The food product may contain a single type of oil or multiple types of oil. The oil may include vegetable oil, algal oil, palm fruit oil, coconut oil, cottonseed oil, mango oil, rice bran oil, flaxseed oil, canola oil, olive oil, soybean oil, sunflower oil, wheat oil, corn oil, barley oil, fish oil, or any combinations thereof.

The unicellular organism-containing product may be mixed or combined with one or more organic acids to generate the food product. The organic acids may preserve the food product and/or alter the flavor of the food product. The organic acids may alter the taste or flavor profile of the food product. The organic acids may be plant derived acids or animal derived acids. The organic acids may include, but are not limited to, lactic acid, glycolic acid, tricarboxylic acids (e.g., citric acid), dicarboxylic acids (e.g., succinic acid or tartaric acid), sorbic acid, caffeic acid, benzoic acid, malic acid, propionic acid, acetic acid, or any combination thereof.

The unicellular organism-containing product may be mixed or combined with one or more flavoring agents to generate the food product. Examples of flavoring agents include yogurt, meat, meat digest, vegetable broth, rice bran, fruit, vegetable, or salt. A flavoring agent may be a natural or artificial flavoring agent. Flavoring agents may include flavoring molecules and/or flavoring precursors such as carbohydrates, sugars, nucleotides, nucleosides, free fatty acids, amino acids and/or amino acid derivatives, vitamins, minerals, antioxidants, or any combination thereof. Carbohydrates and/or sugars may include, but are not limited to, glucose, fructose, ribose, sucrose, arabinose, inositol, maltose, molasses, maltodextrin, glycogen, glycol, galactose, lactose, ribitol, amylose, amylopectin, xylose, or any combination thereof. Nucleotides and/or nucleosides may include, but are not limited to, inosine, inosine monophosphate, guanosine, guanosine monophosphate, adenosine, adenosine monophosphate, or any combination thereof. Free fatty acids may include, but are not limited to, arachidic acid, behenic acid, caprylic acid, capric acid, cerotic acid, erucic acid, lauric acid, linoleic acid, myristic acid, palmitic acid, palmitoleic acid, stearic acid, lignoceric acid, or any combination thereof. Amino acids and/or amino acid derivatives may include, but are not limited to, cysteine, cystine, cysteine sulfoxide, allicin, selenocystein, methionine, isoleucine, leucine, lysine, phenylalanine, threonine, tryptophan, 5-hydroxytryptophan, valine, arginine, histidine, alanine, asparagine, aspartate, glutamate, glutamine, glycine, proline, serine, tyrosine, taurine, or any combination thereof. Amino acids may be added to the food product as free amino acids or as amino acid derivatives. For example, any amino acid may be added to the food product as a free amino acid (e.g., pre-digested amino acids without other functional groups of chemical moieties). Flavoring agents may include, but are not limited to retinol, retinal, beta-carotene, thiamine, riboflavin, niacin, niacinamide, nicotinamide, riboside, pantothenic acid, pyridoxine, pyridoxamine, pyridoxal, biotin, folates, cyanocobalamin, hydroxocobalamin, methylcobalamin, adenosylcobalamin, ascorbic acid, cholecalciferol, ergocalciferol, tocopherols (e.g., alpha-tocopherol), tocotrienols, phylloquinone, menaquinones, potassium, chlorine, sodium, calcium, phosphorus, magnesium, iron, zinc, manganese, copper, iodine, chromium, molybdenum, selenium, cobalt, or any combination thereof. Antioxidants may include, but are not limited to, beta-carotene, alpha-tocopherol, caffeic acid, propyl gallate, epigallocatechin gallate, or any combination thereof.

The unicellular organism-containing product may be mixed or combined with a variety of additives to generate the food product. The additives may include vitamin supplements, mineral supplements, proteins (e.g., proteins derived from plant or animal sources), texture agents (e.g., an agent that provides a given texture to a food product), coloring agents (e.g., an agent that provides a given color to a food product), and/or preservatives (e.g., an agent that preserves the food product). The additives may include taurine, carnitine, sodium ascorbate, vitamin A acetate, vitamin B12, vitamin D-3, vitamin E, beta-carotene, choline chloride, d-calcium pantothenate, folic acid, menodione sodium bisulfite complex, niacin supplement, pyridoxine hydrochloride, riboflavin supplement, thiamine minonitrate, dicalcium phosphate, calcium carbonate, calcium iodate, cobalt carbonate, cobalt proteinate, copper proteinate, copper sulfate, ferrous sulfate, iron proteinate, manganese proteinate, manganese sulfate, potassium chloride, sodium selenite, zinc oxide, zinc proteinate, zinc sulfate, or any combination thereof. Preservatives may include, but are not limited to, butylated hydroxyanisole, butylated hydroxytoluene, ethoxyquin, rosemary extract, sodium propionate, vitamin E, or any combination thereof.

The unicellular organism-containing product may be mixed or combined with one or more iron complexing molecules to generate the food product. The iron complexing molecules may add synthetic, meat-like flavors and aromas to the food product. The iron complexing molecules may be heme, heme-containing proteins, porphyrin, porphyrinogen, chlorin, bacteriochlorophyll, chlorophyllin, bacteriochlorin, isobacteriochlorin, or any combination thereof. The iron complexing molecules may be derived from plants, fungi, bacteria, insects, animals, or any combination thereof. The iron complexing molecules may be derived from a single source or may be derived from multiple sources. In an example, the iron complexing molecule is a heme or heme-containing protein. The heme or heme-containing protein may be derived from plants, fungi, bacteria, insects, animals, or any combination thereof. The heme or heme-containing protein may be derived from a single source or may be derived from multiple sources. The food product may contain, by weight, greater than or equal to about 0.05%, 0.1%, 0.25%, 0.5%, 0.75%, 1%, 1.5%, 2%, 2.5%, 5%, 10%, or more iron complexing molecules (e.g., heme-containing protein). The food product may contain, by weight, less than or equal to about 10%, 5%, 2.5%, 2%, 1.5%, 1%, 0.75%, 0.5%, 0.25%, 0.1%, 0.05%, or less iron complexing molecules (e.g., heme-containing protein). The food product may contain from about 0.05% to 0.1%, 0.05% to 0.25%, 0.05% to 0.5%, 0.05% to 0.75%, 0.05% to 1%, 0.05% to 1.5%, 0.05% to 2%, 0.05% to 2.5%, 0.05% to 5%, or 0.05% to 10% iron containing molecule (e.g., heme-containing protein).

The unicellular organism-containing product may be mixed or combined with one or more of taurine and carnitine to generate the food product. The taurine and carnitine may be nutritional supplements. The food product may contain taurine, carnitine, or a combination of both taurine and carnitine. The taurine or carnitine may be added as free amino acids (e.g., pre-digested amino acids without other functional groups of chemical moieties) or may be added as a derivative of taurine or carnitine. The food product may comprise greater than or equal to about 10 milligrams (mg), 20 mg, 30 mg, 40 mg, 50 gm, 75 mg, 100 mg, 125 mg, 150 mg, 200 mg, 300 mg, 400 mg, 500 mg, 600 mg, 700 mg, 800 mg, 900 mg, 1000 mg, or more taurine per kilogram of food product. The food product may comprise less than or equal to about 1000 mg, 900 mg, 800 mg, 700 mg, 600 mg, 500 mg, 400 mg, 300 mg, 200 mg, 150 mg, 125 mg, 100 mg, 75 mg, 50 mg, 40 mg, 30 mg, 20 mg, 10 mg, or less taurine per kilogram of food product. The food product may comprise from about 10 mg to 20 mg, 10 mg to 30 mg, 10 mg to 40 mg, 10 mg to 50 mg, 10 mg to 75 mg, 10 mg to 100 mg, 10 mg to 125 mg, 10 mg to 150 mg, 10 mg to 200 mg, 10 mg to 300 mg, 10 mg to 400 mg, 10 mg to 500 mg, 10 mg to 600 mg, 10 mg to 700 mg, 10 mg to 800 mg, 10 mg to 900 mg, or 10 mg to 1000 mg per kilogram of food product. The food product may comprise greater than or equal to 5 mg, 10 mg, 20 mg, 30 mg, 40 mg, 50 mg, 75 mg, 100 mg, 125 mg, 150 mg, 175 mg, 200 mg, 300 mg, 400 mg, 500 mg, or more carnitine per 100 grams of food product. The food product may comprise less than or equal to 500 mg, 400 mg, 300 mg, 200 mg, 175 mg, 150 mg, 125 mg, 100 mg, 75 mg, 50 mg, 40 mg, 30 mg, 20 mg, 10 mg, 5 mg, or less per 100 grams of food product. The food product may comprise from about 5 mg to 10 mg, 5 mg to 20 mg, 5 mg to 30 mg, 5 mg to 40 mg, 5 mg to 50 mg, 5 mg to 75 mg, 5 mg to 100 mg, 5 mg to 125 mg, 5 mg to 150 mg, 5 mg to 175 mg, 5 mg to 200 mg, 5 mg to 300 mg, 5 mg to 400 mg, or 5 mg to 500 mg per 100 grams of food product.

A mixture comprising the unicellular organism-containing product (e.g., fungus-containing product) and other ingredients may be heated (e.g., cooked) for a period of time to generate the food product. The mixture may be cooked by extrusion (e.g., heat-expanded), baking, pressure cooking, or any other cooking method. The mixture may be heated at a temperature of greater than or equal to about 50° C., 75° C., 100° C., 125° C., 150° C., 175° C., 200° C., 225° C., 250° C., or more. The mixture may be heated at a temperature of less or equal to about 250° C., 225° C., 200° C., 175° C., 150° C., 125° C., 100° C., 75° C., 50° C., or less. The mixture may be heated from about 50° C. to 75° C., 50° C. to 100° C., 50° C. to 125° C., 50° C. to 150° C., 50° C. to 175° C., 50° C. to 200° C., 50° C. to 225° C., or 50° C. to 250° C. In an example, the mixture is heated at a temperature of greater than or equal to about 150° C. In an example, the mixture is heated at a temperature of greater than or equal to about 175° C. In an example, the mixture is heated at a temperature from about 150° C. to 175° C. The heating may cook the mixture and/or may pasteurize the mixture. The mixture may be heated in a wet or humid environment (e.g., steamed) or in a dry environment (e.g., baked). The heating environment may have a humidity of greater than or equal to about 20%, 30%, 40%, 50%, 60%, 70%, 80%, 90%, or more. The heating environment may have a humidity less than or equal to about 90%, 80%, 70%, 60%, 50%, 40%, 30%, 20%, or less. The heating environment may have a humidity from about 20% to 30%, 20% to 40%, 20% to 50%, 20% to 60%, 20% to 70%, 20% to 80%, or 20% to 90%. The humidity of the heating environment may be the ambient humidity or the humidity may be artificially altered (e.g., as in a vacuum oven or pressure cooker). In an example, the mixture is heated at a temperature of greater than 150° C. in ambient humidity (e.g., from 40% to 80% humidity). In an example, the mixture is heated at a temperature of greater than 175° C. in ambient humidity (e.g., from 40% to 80% humidity).

The mixture may be heated at an ambient pressure, a high pressure, or a lower pressure. The ambient pressure may be the pressure at a given altitude on a given day. For example, the ambient pressure at sea level may be higher than the ambient pressure at elevation. The ambient pressure may be greater than or equal to about 0.4 atmospheres (atm), 0.5 atm, 0.6 atm, 0.7 atm, 0.8 atm, 0.9 atm, 1 atm, or more. The ambient pressure may be less than or equal to about 1 atm, 0.9 atm, 0.8 atm, 0.7 atm, 0.6 atm, 0.5 atm, 0.4 atm, or less. The ambient pressure may be from about 0.4 atm to 0.5 atm, 0.4 atm to 0.6 atm, 0.4 atm to 0.7 atm, 0.4 atm to 0.8 atm, 0.4 atm to 0.9 atm, or 0.4 atm to 1 atm. The high pressure of greater than or equal to about 1.2 atm, 1.5 atm, 2 atm, 4 atm, 6 atm, 8 atm, 10 atm, or more. The high pressure may be from about 1.2 atm to 1.5 atm, 1.2 atm to 2 atm, 1.2 atm to 4 atm, 1.2 atm to 6 atm, 1.2 atm to 8 atm, or 1.2 atm to 10 atm. The low pressure may be a vacuum. The low pressure may be less than or equal to about 1 atm, 0.9 atm, 0.8 atm, 0.7 atm, 0.6 atm, 0.5 atm, 0.4 atm, 0.3 atm, 0.2 atm, 0.1 atm, or less. The low pressure may be from about 0.1 atm to 0.2 atm, 0.1 atm to 0.3 atm, 0.1 atm to 0.4 atm, 0.1 atm to 0.5 atm, 0.1 atm to 0.6 atm, 0.1 atm to 0.7 atm, 0.1 atm to 0.8 atm, or 0.1 atm to 0.9 atm. In an example, the mixture is heated at ambient temperature. In an example, the mixture is heated at a high pressure of greater than or equal to 1.2 atm. In an example, the mixture is heated at a high pressure of greater than or equal to 1.5 atm. In an example, the mixture is heated at a high pressure of greater than or equal to 2 atm. In an example, the mixture is heated at a low pressure of less than or equal to 0.8 atm. In an example, the mixture is heated at a low pressure of less than or equal to 0.5 atm.

The mixture may be heated for a period of time to produce the food product. The period of time may be greater than or equal to 5 seconds (s), 10 s, 20 s, 30 s, 1 minute (min), 2 min, 3 min, 5 min, 8 min, 10 min, 15 min, 20 min, 25 min, 30 min, 45 min, 60 min, or more. The period of time may be less than or equal to 60 min, 45 min, 30 min, 25 min, 20 min, 15 min, 10 min, 8 min, 5 min, 3 min, 2 min, 1 min 30 s, 20 s, 10 s, 5 s, or less. The time period may be from about 5 s to 10 s, 5 s to 20 s, 5 s to 30 s, 5 s to 1 min, 5 s to 2 min, 5 s to 3 min, 5 s to 5 min, 5 s to 8 min, 5 s to 10 min, 5 s to 15 min, 5 s to 20 min, 5 s to 25 min, 5 s to 30 min, 5 s to 45 min, or 5 s to 60 min. In an example, the mixture is heated from about 5 min to 30 minutes. In an example, the mixture is heated from about 10 minutes to 30 minutes. In an example, the mixture is heated from about 20 minutes to 30 minutes. In an example, the mixture is heated at a temperature of greater than or equal to about 150° C. for about 25 minutes to 35 minutes. In an example, the mixture is heated at a temperature of greater than or equal to about 175° C. for about 15 minutes to 25 minutes.

Heating the mixture may reduce the water content of the food product. Alternatively, or in addition to, heating the mixture may maintain or increase the water content of the food product. In an example, the mixture is a wet product and heating minimally changes or increases the water content. In an example, the mixture is a wet product and heating reduces the water content. The food product may be a wet food product and have a water content of greater than or equal to about 30%, 40%, 50%, 60%, 70%, 80%, 90%, or more. The wet food product may have a water content of less than or equal to about 90%, 80%, 70%, 60%, 50%, 40%, or less. The wet food product may have a water content from about 30% to 40%, 30% to 50%, 30% to 60%, 30% to 70%, 30% to 80%, or 30% to 90%. The food product may be a semi-wet food product. The semi-wet food product may have a water content of greater than or equal to 15%, 20%, 25%, or 30%. The semi-wet food product may have a water content of less than or equal to 30%, 25%, 20%, 15%, or less. The semi-wet food product may have a water content from about 15% to 20%, 15% to 25%, or 15% to 30%. The food product may be a dry food product. The dry food product may have a water content of less than or equal to about 15%, 10%, 8%, 6%, 4%, 2%, 1%, or less. The dry food product may have a water content of greater than or equal to 1%, 2%, 4%, 6%, 8%, 10%, or more. The dry food product may have a water content from about 1% to 2%, 1% to 4%, 1% to 6%, 1% to 8%, 1% to 10%, or 1% to 15%. In an example, the food product is a semi-wet food product with a water content of from 15% to 30%. In an example, the food product is a semi-wet or dry food product and has a water content of less than or equal to 30%. In an example, the food product is a dry food product with a water content of less than or equal to 15%.

The heated mixture may be an intermediate product. The intermediate product may be further processed to generate the food product. The intermediate product may or may not be heated. The intermediate product may be further processed and followed by heating. The intermediate product may be heated and then further processed. Further processing may include, but is not limited to, extrusion, grinding, shaping, compacting, molding (e.g., using a mold to impart a given shape), cutting (e.g., cutting with a knife, blade or sharp edge), or any other physical process. In an example, the food product is an animal treat that is shaped prior to heating. In another example, the food product is an animal treat that is shaped and not heated. In another example, the food product is a kibble that is extruded prior to heat treatment. In another example, the intermediate product is ground or crushed after heating to form a granulated food product.

Food Products Containing Single-Cell Proteins

Single-cell proteins may be used in food products for human and animal consumption. Food products may include foods and supplements for human consumptions. Food products may include animal foods, such as foods for companion animals or foods for livestock. Foods for companion animals may include, but are not limited to, dog food, cat food, rodent food, or rabbit food. The animal may be a domesticated animal. The animal may be a zoo animal. The food product may be a meat-like (or synthetic meat) product. The meat-like (e.g., synthetic) product may simulate the taste, texture, and cooking profile of meat (e.g., bovine, fowl, or porcine derived meats). The food product may be consumed raw or after cooking. The food product may contain additional ingredients such as, but not limited to, flours, oils, other proteins, vitamin supplements and mineral supplements, flavoring agents, carbohydrates, volatilizing compounds, taurine, carnitine, heme and heme-containing proteins, organic acids, and/or coloring agents. In an example, the meat-like (or synthetic meat) food product comprises, by weight, at least about 10% or one or more microbial proteins, from 0.1% to 5% of one or more heme-containing proteins, and taurine and/or carnitine as free amino acids. The food product may include animal-derived compounds (e.g., fat, flesh, blood, milk, eggs, rennet, etc.). In an example, the food product does not include animal-derived compounds (e.g., fat, flesh, blood, milk, eggs, rennet, etc.).

In an aspect, the present disclosure provides a food product for consumption. The food product may be for human or animal consumption. In an example, the food product is for animal consumption. The food product may include (i) protein at a protein content of at least about 16% by dry weight and (ii) one or more members selected from the group consisting of a flour, an oil, a flavoring agent, and a nutritional supplement. The protein may include at least about 50% by dry weight of an amino acid sequence encoded by one or more fungal genomes. The food product may have a water content that is less than or equal to about 30% water by weight.

In another aspect, the present disclosure provides a food product for consumption. The food product may be for human or animal consumption. In an example, the food product is for animal consumption. The food product may comprise (i) greater than 3% fungus-containing product by wet weight and (ii) one or more members selected from the group consisting of a flour, an oil, a flavoring agent, and a nutritional supplement. The fungus-containing may comprise at least about 4% by dry weight ribonucleic acids encoded by one or more fungal genomes. The food product may not contain protein from an animal (e.g., does not contain protein comprising an amino acid sequence encoded by an animal genome).

The food product may include single-cell proteins, plant-derived proteins, animal-sourced proteins, insect-sourced proteins, or any combination thereof. The food product may contain greater than or equal to about 10%, 20%, 30%, 40%, 50%, or more total protein on a dry matter basis. The total protein may contain greater than or equal to about 20%, 30%, 40%, 50%, 60%, 70%, 80%, 90%, or more single-cell protein. The total protein may contain less than or equal to about 80%, 70%, 60%, 50%, 40%, less than 30%, 20%, 10%, 5%, or less of plant proteins, animal proteins, insect proteins, or combinations thereof.

The unicellular organism-containing product (e.g., fungus-containing protein) may be a whole cell, a protein concentrate, or a protein isolate derived from unicellular growth (e.g., microbial fermentation). The unicellular organism-containing product may be derived from a fungal cell, a yeast cell, a bacterial cell, an algae cell, a synthetically grown mammalian cell, or a synthetically grown animal cell. In an example, the unicellular organism-containing product is derived from fungal cells, eubacteria cells, archaebacterial cells, or combinations thereof. The unicellular organism-containing product may include proteins from a single microbial source for from multiple microbial sources. In an example, the microbial protein includes a mixture of fungal and bacterial proteins. The unicellular organism-containing product (e.g., fungus-containing product) may comprise greater than or equal to about 20%, 30%, 40%, 50%, 60%, 70%, 80%, or more whole cells (e.g., fungal cells) on a dry matter basis. The fungal cells may include, but are not limited to *Aspergillus oryzae, Fusarium venenatum, Geotrichum candidum, Penicillium camemberti, Penicillium roqueforti, Saccharomyces cerevisiae* or a genetic derivative thereof. The unicellular organism-containing product may be a bacteria-containing product comprising bacterial cells and/or bacterial protein. The bacterial cell may include, but are not limited to *Bifidobacterium bifidum, Lactobacillus acidophilus, Lactobacillus casei, Lactobacillus delbrueckii* subspecies *bulgaricus, Lactobacillus rhamnosus Streptococcus thermophiles*, and/or a genetic derivative thereof. In an example, the food product contains one or more bacteria selected from the group consisting of *Bifidobacterium bifidum, Lactobacillus acidophilus, Lactobacillus casei, Lacto-*

*bacillus delbrueckii* subspecies *bulgaricus, Lactobacillus rhamnosus Streptococcus thermophiles*, and a derivative thereof. In an example, the food product contains both fungal and bacterial cells and/or proteins. A fungal or bacterial protein may include one or more proteins comprising an amino acid sequence encoded by a fungal or bacterial genome.

The food product may contain a unicellular organism containing product that is a whole cell product. The whole cells may be disposed on a surface of a support media (e.g., starch structure). Alternatively, or in addition to, the whole cells may not be disposed on a surface of a support media. The whole cell product may contain greater than or equal to about 40%, 50%, 60%, 70%, 80%, 90%, or more whole cells by weight. The whole cell product may contain from about 40% to 60%, 40% to 70%, 40% to 80%, or 40% to 90% whole cells. The whole cell product may make up greater than or equal to about 20%, 30%, 40%, 50%, 60%, 70%, 80%, 90%, or more of the food product on a dry matter basis. The whole cell product may make up from about 20% to 40%, 20% to 50%, 20% to 60%, 20% to 70%, 20% to 80%, or 20% to 90% of the food product on a dry matter basis. In an example, the whole cell product is a fungus-containing product and the fungus-containing product makes up greater than 30% of the food product by dry weight. In an example, the whole cell product is a fungus-containing product and the fungus-containing product makes up greater than 40% of the food product by dry weight. In an example, the whole cell product is a fungus-containing product and the fungus-containing product makes up greater than 50% of the food product by dry weight. In an example, the whole cell product is a fungus-containing product and the fungus-containing product makes up greater than 60% of the food product by dry weight.

The food product may contain a unicellular organism containing product that is a protein concentrate. The protein concentrate may contain greater than or equal to about 40%, 50%, 60%, 70%, 80%, or more protein on a dry matter basis. The protein concentrate may contain from about 40% to 50%, 40% to 60%, 40% to 70%, 40% to 90%, or 40% to 90% protein on a dry matter basis. In an example, the protein concentrate comprises from 60% to 90% protein by dry weight. The protein concentrate may be further purified to remove excess nucleic acid molecules. The protein concentrate may be added to a food product for human or animal consumption. The protein concentrate may make up greater than or equal to about 20%, 30%, 40%, 50%, 60%, 70%, 80%, 90%, or more of the food product on a dry matter basis. The protein concentrate may make up from about 20% to 40%, 20% to 50%, 20% to 60%, 20% to 70%, 20% to 80%, or 20% to 90% of the food product on a dry matter basis. In an example, the protein concentrate is a fungal protein concentrate and the fungal protein concentrate makes up greater than or equal to 30% of the food product by dry weight. In an example, the protein concentrate is a fungal protein concentrate and the fungal protein concentrate makes up greater than or equal to 40% of the food product by dry weight. In an example, the protein concentrate is a fungal protein concentrate and the fungal protein concentrate makes up greater than or equal to 50% of the food product by dry weight. In an example, the protein concentrate is a fungal protein concentrate and the fungal protein concentrate makes up greater than or equal to 60% of the food product by dry weight.

The food product may contain a unicellular organism containing product that is a protein isolate. The protein isolate may contain greater than or equal to about 80%, 85%, 90%, 95%, 98%, or more protein on a dry matter basis. The protein isolate may contain from about 80% to 85%, 80% to 90%, 80% to 95%, or 80% to 98% protein on a dry matter basis. The protein isolate may be further purified to remove excess nucleic acid molecules. The protein isolate may be added to a food product. The protein isolate may make up greater than or equal to about 20%, 30%, 40%, 50%, 60%, 70%, 80%, 90%, or more of the food product on a dry matter basis. The protein isolate may make up from about 20% to 40%, 20% to 50%, 20% to 60%, 20% to 70%, 20% to 80%, or 20% to 90% of the food product on a dry matter basis. In an example, the protein isolate is a fungal protein isolate and the fungal protein isolate makes up greater than or equal to 30% of the food product by dry weight. In an example, the protein isolate is a fungal protein isolate and the fungal protein isolate makes up greater than or equal to 40% of the food product by dry weight. In an example, the protein isolate is a fungal protein isolate and the fungal protein isolate makes up greater than or equal to 50% of the food product by dry weight. In an example, the protein isolate is a fungal protein isolate and the fungal protein isolate makes up greater than or equal to 60% of the food product by dry weight.

The food product may contain a unicellular organism-containing product that comprises whole cells or purified proteins. The unicellular organism-containing product may contain a single type of unicellular organism or protein from a single unicellular organism or may contain multiple different types of unicellular organisms or proteins from the multiple different types of unicellular organisms. The unicellular organism-containing product may comprise a mixture of types of fungi, bacteria, algae, animal cells, or any combination thereof. In an example, the unicellular organism-containing product is a fungus-containing product and the fungus-containing product comprises one or more different types of fungus. In an example, the fungus-containing product includes *Aspergillus oryzae* and *Saccharomyces cerevisiae*. The *Aspergillus oryzae* and *Saccharomyces cerevisiae* may be present in the fungus-containing product at a ratio of greater than or equal to about 1:1, 1:2, 1:3, 1:4, 1:5, 1:6, 1:7, 1:8, 1:9, 1:10, or more. The *Aspergillus oryzae* and *Saccharomyces cerevisiae* may be present in the fungus-containing product at a ratio of less than or equal to about 1:10, 1:9, 1:8, 1:7, 1:6, 1:5, 1:4, 1:3, 1:2, 1:1, or less. The *Aspergillus oryzae* and *Saccharomyces cerevisiae* may be present in the fungus-containing product at a ratio from about 1:1 to 1:2, 1:1 to 1:3, 1:1 to 1:4, 1:1 to 1:5, 1:1 to 1:6, 1:1 to 1:7, 1:1 to 1:8, 1:1 to 1:9, 1:1 to 1:10, 1:10 to 1:9, 1:10 to 1:8, 1:10 to 1:7, 1:10 to 1:6, 1:10 to 1:5, 1:10 to 1:4, 1:10 to 1:3, 1:10 to 1:2, or 1:10 to 1:1. In an example, *Aspergillus oryzae* and *Saccharomyces cerevisiae* are present at a ratio from about 1:5 to 1:2.

The food product may comprise a unicellular organism-containing product and one or more ingredients to generate the food product. The one or more ingredients may be wet ingredients or dry ingredients. The unicellular organism-containing product may be a wet ingredient or a dry ingredient. The food product may comprise greater than or equal to about 3%, 4%, 6%, 8%, 10%, 15%, 20%, 25%, 30%, 40%, 50%, 60%, 70%, 80%, 90%, or more unicellular organism-containing product by wet weight. The food product may comprise less than or equal to about 90%, 80%, 70%, 60%, 50%, 40%, 30%, 25%, 20%, 15%, 10%, 8%, 6%, 4%, 3%, or less unicellular organism-containing product by wet weight. The food product may comprise from about 3% to 4%, 3% to 6%, 3% to 8%, 3% to 10%, 3% to 15%, 3% to 20%, 3% to 25%, 3% to 30%, 3% to 40%, 3% to 50%, 3% to 60%, 3% to 70%, 3% to 80%, or 3% to 90% of the unicellular organism-containing product. In an example, the unicellular organism-containing product is a fungus-containing product and the food product contains at least 3% fungus-containing product by wet weight. In an example, the fungus-containing product is made up of *Aspergillus oryzae* and the food product comprises at least 3% *Aspergillus oryzae* by wet weight. In another example, the fungus-containing product is made up of *Aspergillus oryzae* and *Saccharomyces cerevisiae* and the food product comprises at least 3% *Aspergillus oryzae* by wet weight. In another example, the fungus-containing product is made up of *Aspergillus oryzae* and *Saccharomyces cerevisiae* and the food product comprises at least 6% *Aspergillus oryzae* by wet weight. In another example, the fungus-containing product is made up of *Aspergillus oryzae* and *Saccharomyces cerevisiae* and the food product comprises at least 8% *Aspergillus oryzae* by wet weight. In another example, the fungus-containing product is made up of *Aspergillus oryzae* and *Saccharomyces cerevisiae* and the food product comprises at least 10% *Aspergillus oryzae* by wet weight.

The food product may include a unicellular organism-containing product that is mixed with other ingredients to form a homogenous or semi-homogenous food product. Alternatively, or in addition to, the food product may comprise a coating or sprayed on layer of the unicellular organism-containing product. In an example, the unicellular organism-containing product (e.g., fungus-containing product) is mixed with other ingredients to form a homogenous or semi-homogenous food product and is not a spray or coating on an outer surface of the food product.

In an example, a food product for human, animal, or companion animal consumption comprises whole animal cells, protein concentrate derived from animal cells, protein isolate derived from animal cells, or any combination thereof. The animal cells may be synthetically cultured outside of an animal. The food product may comprise greater than or equal to about 10%, 20%, 30%, 40%, 50%, 60%, 70%, 80%, 90%, or more of whole animal cells. The food product may comprise less than or equal to about 90%, 80%, 70%, 60%, 50%, 40%, 30%, 30%, 10%, or less of whole animal cells. The food product may comprise from about 10% to 20%, 10% to 30%, 10% to 40%, 10% to 50%, 10% to 60%, 10% to 70%, 10% to 80%, or 10% to 90% of whole animal cells. In an example, the food product contains no whole animal cells. In another example, the food product does not contain an animal protein. In another example, the food product does not contain an animal product (e.g., animal oil, cell, etc.).

The food product may comprise a unicellular organism-containing product (e.g., whole cell, protein concentrate, or protein isolate) with a native or reduced concentration of nucleic acid molecules (e.g., ribonucleic acid (RNA) or deoxyribonucleic acid (DNA)). Nucleic acid molecules in the food product may alter the taste of the food product. For example, RNA may degrade and impart an umami-like flavor to the food product. The native (e.g., without removal) amount of RNA in the unicellular organism-containing product may be greater than or equal to about 2%, 3%, 4%, 5%, 6%, 7%, 8%, 9%, 10%, 15%, 20%, or more on a dry matter basis. In an example, the unicellular organism-containing product may contain greater than about 4% RNA on a dry matter basis. In an example, the unicellular organism-containing product may contain greater than about 6% RNA on a dry matter basis. In an example, the unicellular organism-containing product may contain greater than about 8% RNA on a dry matter basis. In an example, not removing or reducing the concentration of nucleic acid molecules (e.g., RNA and DNA) give the food product a more umami or cooked meat or broth flavor of the food product. In an example, the unicellular organism-containing product is processed or treated to remove nucleic acids (e.g., RNA and/or DNA). The unicellular organism-containing product may be processed to reduce the concentration of nucleic acids to less than or equal to about 4% 3%, 2%, 1%, 0.5%, 0.1%, or less by dry weight. The unicellular organism-containing product may be processed to reduce the concentration of RNA to less than or equal to about 4% 3%, 2%, 1%, 0.5%, 0.1%, or less by dry weight. In an example, the unicellular organism-containing product may contain less than about 4% RNA on a dry matter basis. In an example, the unicellular organism-containing product may contain less than 6% RNA on a dry matter basis. In an example, the unicellular organism-containing product may contain less than 8% RNA on a dry matter basis. In an example, removing or reducing the concentration of nucleic acid molecules (e.g., RNA and DNA) reduces an amount of umami or cooked meat or broth flavor of the food product.

The food product may contain plant-derived flours. The flours may be derived from grain products. The food product may contain less than or equal to about 70%, 60%, 50%, 40%, 30%, 20%, 10%, 5%, 4%, 3%, 2%, 1%, or less flour on a dry matter basis. The food product may contain from about 20% to 30%, 20% to 40%, 20% to 50%, 20% to 60%, or 20% to 70% flour on a dry matter basis. In an example, the food product contains from about 30% to 50% flour by dry weight. The food product may contain a single type of flour or multiple types of flour. The flour may include, but is not limited to, wheat flour, flaxseed flour, rice flour, corn flour, corn gluten, corn bran, corn starch, barley flour, sorghum flour, oat flour, potato flour, rye flour, soybean flour, or any combinations thereof.

The food product may contain plant-derived and non-plant derived oils. The food product may contain less than or equal to about 40%, 30%, 20%, 10%, 5%, 4%, 3%, 2%, 1% or less oil on a dry matter basis. The food product may contain from about 1% to 2%, 1% to 3%, 1% to 4%, 1% to 5%, 1% to 10%, 1% to 20%, 1% to 30%, or 1% to 40% oil on a dry matter basis. In an example, the food product contains from about 10% to 20% oil by dry weight. The food product may contain a single type of oil or multiple types of oil. The oil may include vegetable oil, algal oil, palm fruit oil, coconut oil, cottonseed oil, mango oil, rice bran oil, flaxseed oil, canola oil, olive oil, soybean oil, sunflower oil, wheat oil, corn oil, barley oil, fish oil, essential oil, or any combinations thereof.

The food product may contain one or more organic acids. The organic acids may preserve the food product. The organic acids may alter the taste or flavor profile of the food product. The organic acids may be plant derived acids or animal derived acids. The organic acids may include, but are not limited to, lactic acid, glycolic acid, tricarboxylic acids (e.g., citric acid), dicarboxylic acids (e.g., succinic acid or tartaric acid), sorbic acid, caffeic acid, benzoic acid, malic acid, propionic acid, acetic acid, or any combination thereof.

The food product may include flavoring molecules and flavoring precursors that act as flavoring agents. A flavoring agents may be a flavoring molecule(s) and/or flavoring precursor(s). Flavoring agents may include carbohydrates, sugars, nucleic acids (e.g., nucleotides and/or nucleosides), free fatty acids, amino acids and/or derivatives, vitamins, minerals, antioxidants, or any combination thereof. Carbohydrates and sugars may include, but are not limited to, glucose, fructose, ribose, sucrose, arabinose, inositol, maltose, molasses, maltodextrin, glycogen, glycol, galactose, lactose, ribitol, amylose, amylopectin, xylose, or any combination thereof. Nucleic acids may include, but are not limited to, inosine, inosine monophosphate, guanosine, guanosine monophosphate, adenosine, adenosine monophosphate, or any combination thereof. Free fatty acids may include, but are not limited to, arachidic acid, behenic acid, caprylic acid, capric acid, cerotic acid, erucic acid, lauric acid, linoleic acid, myristic acid, palmitic acid, palmitoleic acid, stearic acid, lignoceric acid, or any combination thereof. Amino acids and/or amino acid derivatives may include, but are not limited to, cysteine, cystine, cysteine sulfoxide, allicin, selenocystein, methionine, isoleucine, leucine, lysine, phenylalanine, threonine, tryptophan, 5-hydroxytryptophan, valine, arginine, histidine, alanine, asparagine, aspartate, glutamate, glutamine, glycine, proline, serine, tyrosine, taurine, or any combination thereof. Amino acids may be added to the food product as free amino acids or as amino acid derivatives. For example, any amino acid may be added to the food product as a free amino acid (e.g., pre-digested amino acids without other functional groups of chemical moieties). Flavoring agents may include, but are not limited to retinol, retinal, beta-carotene, thiamine, riboflavin, niacin, niacinamide, nicotinamide, riboside, pantothenic acid, pyridoxine, pyridoxamine, pyridoxal, biotin, folates, cyanocobalamin, hydroxocobalamin, methylcobalamin, adenosylcobalamin, ascorbic acid, cholecalciferol, ergocalciferol, tocopherols (e.g., alpha-tocopherol), tocotrienols, phylloquinone, menaquinones, potassium, chlorine, sodium, calcium, phosphorus, magnesium, iron, zinc, manganese, copper, iodine, chromium, molybdenum, selenium, cobalt, or any combination thereof. Antioxidants may include, but are not limited to, beta-carotene, alpha-tocopherol, caffeic acid, propyl gallate, epigallocatechin gallate, or any combination thereof.

The food product may contain a variety of additives, such as flavoring agents, vitamin supplements, mineral supplements, proteins (e.g., plant or animal derived proteins), texture agents (e.g., an agent that provides a given texture to a food product), coloring agents (e.g., an agent that provides a given color to a food product), or preservatives (e.g., an agent that preserves the food product). Flavoring agents may include yogurt, meat, meat digest, vegetable broth, or rice bran. Flavoring agents may include natural and/or artificial flavoring. The additives may include taurine, carnitine, sodium ascorbate, vitamin A acetate, vitamin B12, vitamin D-3, vitamin E, beta-carotene, choline chloride, dicalcium phosphate, d-calcium pantothenate, folic acid, menodione sodium bisulfite complex, niacin supplement, pyridoxine hydrochloride, riboflavin supplement, thiamine minonitrate, calcium carbonate, calcium iodate, cobalt carbonate, cobalt proteinate, copper proteinate, copper sulfate, ferrous sulfate, iron proteinate, manganese proteinate, manganese sulfate, potassium chloride, sodium selenite, zinc oxide, zinc proteinate, zinc sulfate, or any combination thereof. Preservatives may include, but are not limited to, butylated hydroxyanisole, butylated hydroxytoluene, ethoxyquin, rosemary extract, sodium propionate, vitamin E, or any combination thereof.

The food product may contain iron complexing molecules to add synthetic, meat-like flavors and aromas to the food product. The iron complexing molecules may be heme, heme-containing proteins, porphyrin, porphyrinogen, chlorin, bacteriochlorophyll, chlorophyllin, bacteriochlorin, isobacteriochlorin, or any combination thereof. The iron complexing molecules may be derived from plants, fungi, bacteria, insects, animals, or any combination thereof. The iron complexing molecules may be derived from a single source or may be derived from multiple sources. In an example, the iron complexing molecule is a heme or heme-containing protein. The heme or heme-containing protein may be derived from plants, fungi, bacteria, insects, animals, or any combination thereof. The heme or heme-containing protein may be derived from a single source or may be derived from multiple sources. The food product may contain, by weight, greater than or equal to about 0.05%, 0.1%, 0.25%, 0.5%, 0.75%, 1%, 1.5%, 2%, 2.5%, 5%, 10%, or more iron complexing molecules (e.g., heme-containing protein). The food product may contain, by weight, less than or equal to about 10%, 5%, 2.5%, 2%, 1.5%, 1%, 0.75%, 0.5%, 0.25%, 0.1%, 0.05%, or less iron complexing molecules (e.g., heme-containing protein). The food product may contain from about 0.05% to 0.1%, 0.05% to 0.25%, 0.05% to 0.5%, 0.05% to 0.75%, 0.05% to 1%, 0.05% to 1.5%, 0.05% to 2%, 0.05% to 2.5%, 0.05% to 5%, 0.05% to 10% iron containing molecule (e.g., heme-containing protein).

The food product may contain taurine and/or carnitine as examples of nutritional supplements. The food product may contain taurine, carnitine, or a combination of both taurine and carnitine. The taurine or carnitine may be added as free amino acids (e.g., pre-digested amino acids without other functional groups of chemical moieties) or may be added as a derivative of taurine or carnitine. The food product may comprise greater than or equal to about 10 milligrams (mg), 20 mg, 30 mg, 40 mg, 50 gm, 75 mg, 100 mg, 125 mg, 150 mg, 200 mg, 300 mg, 400 mg, 500 mg, 600 mg, 700 mg, 800 mg, 900 mg, 1000 mg, or more taurine per kilogram of food product. The food product may comprise less than or equal to about 1000 mg, 900 mg, 800 mg, 700 mg, 600 mg, 500 mg, 400 mg, 300 mg, 200 mg, 150 mg, 125 mg, 100 mg, 75 mg, 50 mg, 40 mg, 30 mg, 20 mg, 10 mg, or less taurine per kilogram of food product. The food product may comprise from about 10 mg to 20 mg, 10 mg to 30 mg, 10 mg to 40 mg, 10 mg to 50 mg, 10 mg to 75 mg, 10 mg to 100 mg, 10 mg to 125 mg, 10 mg to 150 mg, 10 mg to 200 mg, 10 mg to 300 mg, 10 mg to 400 mg, 10 mg to 500 mg, 10 mg to 600 mg, 10 mg to 700 mg, 10 mg to 800 mg, 10 mg to 900 mg, or 10 mg to 1000 mg per kilogram of food product. The food product may comprise greater than or equal to 5 mg, 10 mg, 20 mg, 30 mg, 40 mg, 50 mg, 75 mg, 100 mg, 125 mg, 150 mg, 175 mg, 200 mg, 300 mg, 400 mg, 500 mg, or more carnitine per 100 grams of food product. The food product may comprise less than or equal to 500 mg, 400 mg, 300 mg, 200 mg, 175 mg, 150 mg, 125 mg, 100 mg, 75 mg, 50 mg, 40 mg, 30 mg, 20 mg, 10 mg, 5 mg, or less per 100 grams of food product. The food product may comprise from about 5 mg to 10 mg, 5 mg to 20 mg, 5 mg to 30 mg, 5 mg to 40 mg, 5 mg to 50 mg, 5 mg to 75 mg, 5 mg to 100 mg, 5 mg to 125 mg, 5 mg to 150 mg, 5 mg to 175 mg, 5 mg to 200 mg, 5 mg to 300 mg, 5 mg to 400 mg, or 5 mg to 500 mg per 100 grams of food product.

The food product may be a wet food product, semi-wet food product, or a dry food product. The food product may be a wet food product and have a water content of greater than or equal to about 30%, 40%, 50%, 60%, 70%, 80%, 90%, or more. The wet food product may have a water content of less than or equal to about 90%, 80%, 70%, 60%, 50%, 40%, or less. The wet food product may have a water content from about 30% to 40%, 30% to 50%, 30% to 60%, 30% to 70%, 30% to 80%, or 30% to 90%. The food product may be a semi-wet food product. The semi-wet food product may have a water content of greater than or equal to 15%, 20%, 25%, or 30%. The semi-wet food product may have a water content of less than or equal to 30%, 25%, 20%, 15%, or less. The semi-wet food product may have a water content from about 15% to 20%, 15% to 25%, or 15% to 30%. The food product may be a dry food product. The dry food product may have a water content of less than or equal to about 15%, 10%, 8%, 6%, 4%, 2%, 1%, or less. The dry food product may have a water content of greater than or equal to 1%, 2%, 4%, 6%, 8%, 10%, or more. The dry food product may have a water content from about 1% to 2%, 1% to 4%, 1% to 6%, 1% to 8%, 1% to 10%, or 1% to 15%. In an example, the food product is a semi-wet food product with a water content of from 15% to 30%. In an example, the food product is a semi-wet or dry food product and has a water content of less than or equal to 30%. In an example, the food product is a dry food product with a water content of less than or equal to 15%.

The composition may be formulated for mouthfeel, taste, nutritional value, and shelf life. Mouthfeel of the food product may be determined by structure, dryness, density, adhesiveness, bounce, chewiness, coarseness, cohesiveness, fracturability, graininess, gumminess, hardness, heaviness, moisture adsorption, moisture release, mouthcoating, roughness, slipperiness, smoothness, springiness, uniformity, and viscosity. The food product may have a porous, fibrous, or amorphous structure. In an example, the food product has a fibrous structure. The food product may have a bulk density that is greater than or equal to about 0.3 grams per cubic centimeter ($g/cm^3$), 0.4 $g/cm^3$, 0.5 $g/cm^3$, 0.6 $g/cm^3$, 0.7 $g/cm^3$, 0.8 $g/cm^3$, 1.1 $g/cm^3$, 1.2 $g/cm^3$, 1.3 $g/cm^3$, or greater. The bulk density of the food product may be from about 0.5 $g/cm^3$ to 0.7 $g/cm^3$, 0.5 $g/cm^3$ to 0.8 $g/cm^3$, 0.5 $g/cm^3$ to 0.9 $g/cm^3$, 0.5 $g/cm^3$ to 1.0 $g/cm^3$, 0.5 $g/cm^3$ to 1.1 $g/cm^3$, 0.5 $g/cm^3$ to 1.2 $g/cm^3$, or 0.5 $g/cm^3$ to 1.3 $g/cm^3$. The food product may have a dry density that is greater than or equal to about 0.3 kilograms per cubic meter ($kg/m^3$), 0.4 $kg/m^3$, 0.5 $kg/m^3$, 0.6 $kg/m^3$, 0.7 $kg/m^3$, 0.8 $kg/m^3$, 0.9 $kg/m^3$, 1.0 $kg/m^3$, or more. The dry density of the food product may be from about 0.3 $kg/m^3$ to 0.4 $kg/m^3$, 0.3 $kg/m^3$ to 0.5 $kg/m^3$, 0.3 $kg/m^3$ to 0.6 $kg/m^3$, 0.3 $kg/m^3$ to 0.7 $kg/m^3$, 0.3 $kg/m^3$ to 0.8 $kg/m^3$, 0.3 $kg/m^3$ to 0.9 $kg/m^3$, or 0.3 $kg/m^3$ to 1.0 $kg/m^3$.

The fracturability of the food product may be the force with which the product crumbles, cracks, or shatters. Fracturability may encompass crumbliness, crispness, crunchiness, and brittleness. Cutting force, also called hardness, measurements may be used to assess fracturability. The food product may have a cutting force that is less than or equal to about 15 kilogram-force (kg-f), 10 kg-f, 8 kg-f, 6 kg-f, 5 kg-f, 4 kg-f, 3 kg-f, 2 kg-f, 1 kg-f, or less. The cutting force may be from about 1 kg-f to 2 kg-f, 1 kg-f to 3 kg-f, 1 kg-f to 4 kg-f, 1 kg-f to 5 kg-f, 1 kg-f to 6 kg-f, 1 kg-f to 8 kg-f, 1 kg-f to 10 kg-f, or 1 kg-f to 15 kg-f.

The food product may be stored frozen (e.g., at −20° C.), refrigerated (e.g., 4° C.), or at room temperature (e.g., approximately 25° C.). The food product may have a frozen shelf life of greater than about 6 months, greater than about 1 year, greater than or equal to about 1.5 years, 2 years, 3 years, 4 years, 5 years, or more. The food product may have a refrigerated shelf life greater than or equal to about 1 month, 2 months, 4 months, 6 months, 1 year, 1.5 years, 2 years, 3 years, 4 years, 5 years, or more. The food product stored at room temperature may have a shelf life of greater than or equal to about 2 months, 4 months, 6 months, 1 year, 1.5 years, 2 years, 3 years, 4 years, 5 years, or more.

The food product may be consumed raw (e.g., prior to or without cooking) or the food product may be consumed after cooking. Prior to cooking, the raw food product may have a pink-like color. The red or pink color may mimic the color of raw meat (e.g., beef, pork, chicken, bison, kangaroo, horse, lamb, goat, duck, caribou, carabao, dog, elk, moose, turkey, etc.). During cooking, the red or pink color may change to the off-white or brown color of cooked meat. The food product may undergo a color transition when the internal temperature of the food product is greater than or equal to about 40° C., 50° C., 60° C., 70° C., 80° C., 90° C., 100° C., 120° C., 140° C., 160° C., or more. The food product may undergo a color transition when the internal temperature of the food product is less than or equal to about 160° C., 140° C., 120° C., 100° C., 90° C., 80° C., 70° C., 60° C., 50° C., 40° C., or less. The food product may undergo a color transition when the internal temperature of the food product is from about 40° C. to 50° C., 40° C. to 60° C., 40° C. to 70° C., 40° C. to 80° C., 40° C. to 90° C., 40° C. to 100° C., 40° C. to 120° C., 40° C. to 140° C., or 40° C. to 160° C.

The food product may release volatile compounds during cooking. The volatile compounds may generate an odor profile similar to the odor profile of cooking meat. The volatile compounds released during cooking may alter the flavor of the food product. The food product may release volatile compounds when the temperature is greater than or equal to about 40° C., 50° C., 60° C., 70° C., 80° C., 90° C., 100° C., 120° C., 140° C., 160° C., or more. The food product may release volatile compounds when the temperature of the food product is less than or equal to about 160° C., 140° C., 120° C., 100° C., 90° C., 80° C., 70° C., 60° C., 50° C., 40° C., or less. The food product may release volatile compounds when the internal temperature of the food product is from about 40° C. to 50° C., 40° C. to 60° C., 40° C. to 70° C., 40° C. to 80° C., 40° C. to 90° C., 40° C. to 100° C., 40° C. to 120° C., 40° C. to 140° C., or 40° C. to 160° C.

Volatile compounds may include Phenylacetaldehyde, 1-octen-3-one, 2-n-heptylfuran, 2-thiophenecarboxaldehyde, 3-thiophenecarboxaldehyde, 1-octene, butyrolactone, 2-undecenal, propyl-cyclopropane, methyl-pyrazine, 1-hydroxy-propanone, acetic acid, furfural, 2-decanone, pyrrole, 1-octen-3-ol, 2-acetylthiazole, trans-2-octenal, decanal, benzaldehyde, trans-2-Nonenal, pyrazine, 1-pentanol, trans-2-(2-pentenyl)furan, 1-hexanol, 1-heptanol, dimethyl trisulfide, 2-butenal,2-ethylacetonitrile, trans-2-Hexenal, 4-ethylphenol, 3-octanone, styrene, furan, 3-pentylformic acid, heptyl ester, trans-2-Heptenal, 6-methyl-5-hepten-2-one, n-caproic acid, vinyl ester, 2-ethyl-2-hexenal, 1-hepten-3-ol, 1-ethyl-1-methylcyclopentane, 3-ethyl-2-methyl-1,3-hexadiene, 2-pentyl-thiophene, cis-2-nonenal, 2-n-octylfuran, 2-hexyl-thiophene, 4-cyclopentene-1,3-dione, 1-nonanol, trans-2-decenal, 4-ethyl-benzaldehyde, 1,7-octadien-3-ol, octanoic acid, 2-ethyl-5-methylpyrazine, 1,3-hexadiene, 4-decyne, pentanal, 1-propanol, heptanoic acid, ethanethiol, 2-methyl-1-heptene, trans-4-octene, 2-methyl-2-heptene, pentanoic acid, nonanoic acid, 1,3-dimethylbenzene, toluene, 1-butanol, 2,3,3-trimethylpentane, isopropyl alcohol, 2,2,4,6,6-pentamethyl-heptane, phenol, 1-penten-3-one, dimethyl sulfide, thiirane, trans-2-octen-1-ol, 2,4-dimethyl-1-heptene, 1,3-bis(1,1-dimethylethyl)-benzene, heptane, 4,7-dimethylundecane, 2-nonanone 3-ethyl-2,5-dimethyl-acetophenone, pyrazine, 2-pentanone 1,3,5-cycloheptatriene tridecane, 2-heptanone 2-ethyl-1-hexanol thiophosphoramide, s-methyl ester, 2,3-butanedione 4-methyl-octanoic acid 2-methyl-thiazole, heptanal m-3-(1-methylethoxy)-aminophenylacetylene propanenitrile, nonanal benzene 2,4-bis(1,1-dimethylethyl)-phenol, 2-octanone thiophene 3-ethyl-2,2-dimethylpentane, 2-butanone 2-methyl-furan 3-ethyl-pentane, octanal pyridine 2,3,4-trimethylpentane, 1-octanol fur an 2,4,6-trimethyloctane, 3-ethylcyclopentanone butanal 2,6-dimethyl-nonane, 8-methyl-1-undecene 2-ethyl-furan 2-hexyl-furan, 3-octen-2-one carbon disulfide 4-methyl-5-thiazoleethanol, 2,4-Heptadienal, (E,E)-Furan, 2-hexyl-:2 4-penten-2-one, (Z)-2-heptenal 3-methyl-butanal 4-methylthiazole, 6-methyl-2-heptanone 2-methyl-butanal 2-methyl-3-pentanone, (Z)-4-heptenal methacrolein 2,3-pentanedione, (E,Z)-2,6-nonadienal octane (E)-2-tridecen-1-ol, 3-methyl-2-butenal ethanol 2-thiophenemethanarnine, 2-pentyl-furan 2-methyl-propanal (Z)-2-nonenal, thiazole acetone methyl thiolacetate, (E,E)-2,4-decadienal prop anal methyl ethanoate, hexanoic acid methyl-thiirane isothiazole, 1-ethyl-5-acetaldehyde 3,3-dimethyl-hexane, methylcyclopentene, (E,E)-2,4-nonadienal 2-propenal 4-methyl-heptane, (Z)-2-decenal 2-propyl-furan 2,4-dimethyl-heptane, dihydro-5-pentyl-2(3h)-dihydro-5-propyl-2,3,4-trimethyl-furanone, 2(3H)-furanone heptane, trans-3-nonen-2-one dihydro-3-(2H)-2-methyl-heptane, thiophenone, (E,E)-3,5-octadien-2-one 2,2,6-trimethy 1-decane 2-methyl-3-furanthiol, (Z)-2-octen-1-ol 3,3'-dithiobis[2-methyl-4-amino-1,2, 5-fur an oxadiazole-3-carbo nitrile, 5-ethyldihydro-2(3h)-1-heptene 1,2-benzisothiazolfuranone, or any combination thereof. The food product may release greater than or equal to 1, 2, 3, 4, 5, 6, 7, 8, 9, 10, 15, 20, 30 or more volatile compounds.

The food product may be a shaped and/or molded or non-shaped product. For example, the food product may comprise shaped treats, extruded kibble, or edible granules.

Computer Control Systems

Figure 3:
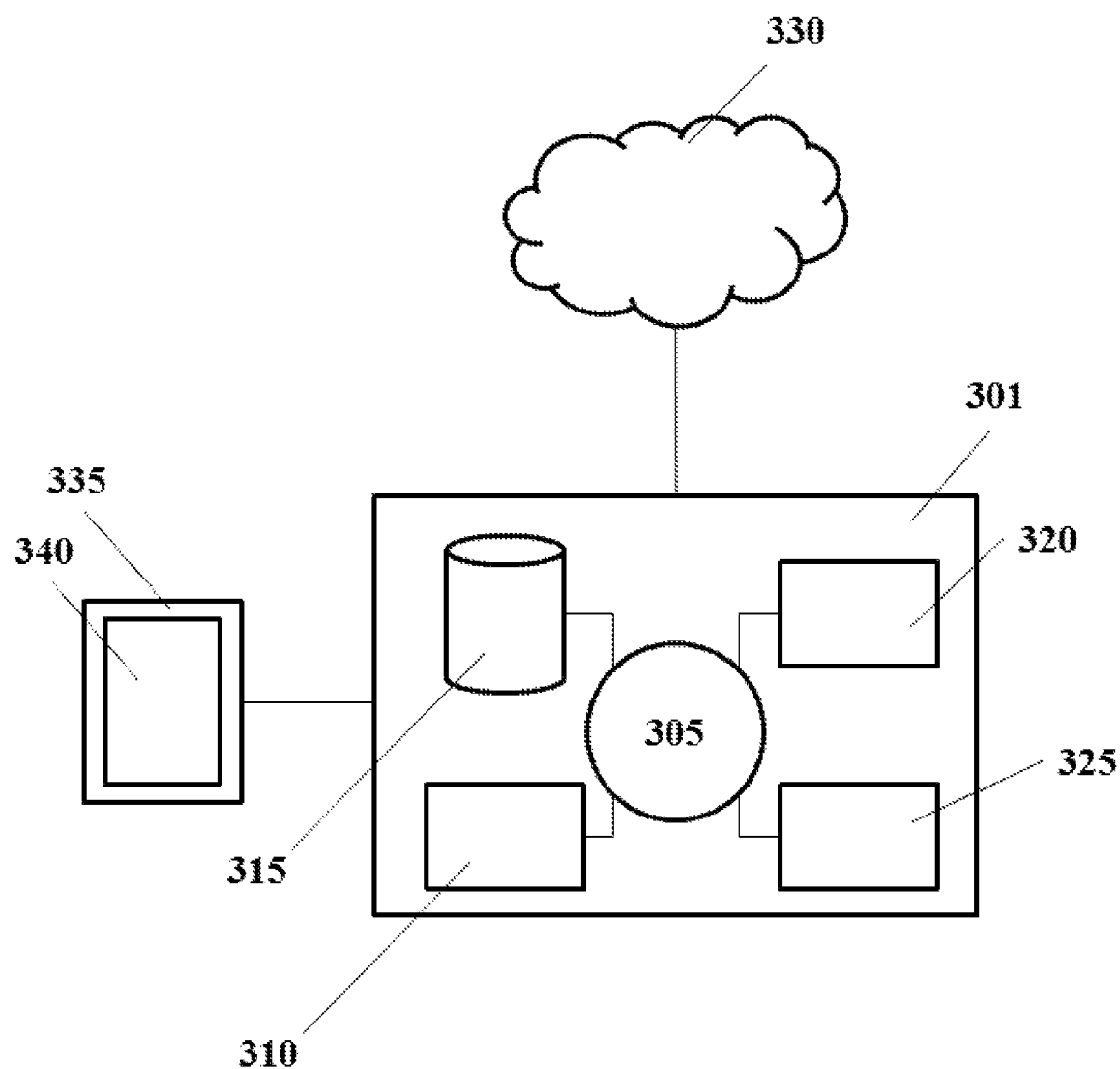
FIG. 3 shows a computer control system that is programmed or otherwise configured to implement methods provided herein.

The present disclosure provides computer control systems that are programmed to implement methods of the disclosure. FIG. 3 shows a computer system 301 that is programmed or otherwise configured to control, direct, or implement the methods described herein. For example, the computer system may be integrated with the reactor, bioreactor, or chemostat. The computer system 301 may regulate various aspects of producing single-cell proteins of the present disclosure, such as, for example, monitoring and controlling the operating conditions of a reactor. The computer system 301 can be an electronic device of a user or a computer system that is remotely located with respect to the electronic device. The electronic device can be a mobile electronic device that is wirelessly connected to a computer system.

The computer system 301 includes a central processing unit (CPU, also "processor" and "computer processor" herein) 305, which can be a single core or multi core processor, or a plurality of processors for parallel processing. The computer system 301 also includes memory or memory location 310 (e.g., random-access memory, read-only memory, flash memory), electronic storage unit b (e.g., hard disk), communication interface 320 (e.g., network adapter) for communicating with one or more other systems, and peripheral devices 325, such as cache, other memory, data storage and/or electronic display adapters. The memory 310, storage unit 315, interface 320 and peripheral devices 325 are in communication with the CPU 305 through a communication bus (solid lines), such as a motherboard. The storage unit 315 can be a data storage unit (or data repository) for storing data. The computer system 301 can be operatively coupled to a computer network ("network") 330 with the aid of the communication interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330, in some cases with the aid of the computer system 301, can implement a peer-to-peer network, which may enable devices coupled to the computer system 301 to behave as a client or a server.

The CPU 305 can execute a sequence of machine-readable instructions, which can be embodied in a program or software. The instructions may be stored in a memory location, such as the memory 310. The instructions can be directed to the CPU 305, which can subsequently program or otherwise configure the CPU 305 to implement methods of the present disclosure. Examples of operations performed by the CPU 305 can include fetch, decode, execute, and writeback.

The CPU 305 can be part of a circuit, such as an integrated circuit. One or more other components of the system 301 can be included in the circuit. In some cases, the circuit is an application specific integrated circuit (ASIC).

The storage unit 315 can store files, such as drivers, libraries and saved programs. The storage unit 315 can store user data, e.g., user preferences and user programs. The computer system 301 in some cases can include one or more additional data storage units that are external to the computer system 301, such as located on a remote server that is in communication with the computer system 301 through an intranet or the Internet.

The computer system 301 can communicate with one or more remote computer systems through the network 330. For instance, the computer system 301 can communicate with a remote computer system of a user (e.g., system operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 301 via the network 330.

Methods as described herein can be implemented by way of machine (e.g., computer processor) executable code stored on an electronic storage location of the computer system 301, such as, for example, on the memory 310 or electronic storage unit 315. The machine executable or machine readable code can be provided in the form of software. During use, the code can be executed by the processor 305. In some cases, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 301, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 301 can include or be in communication with an electronic display 335 that comprises a user interface (UI) 340 for providing, for example, information about the current operation, operation history, and set points of a reactor. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 305. The algorithm can, for example, alter the operating conditions of a reactor in response to an input. Inputs may include, but are not limited to, temperature, pH, dissolved oxygen, rotations per minute or optical density.

EXAMPLES

Animal Treat Example 1

*Aspergillus oryzae* is dried prior to mixing into an animal treat food product to develop a umami flavor. The *Aspergillus oryzae* may be at least partially caramelized during drying. The food product may be generated by combining 15-30 weight % (wt %) dry *Aspergillus oryzae* with 30-50 wt % flour, 0.5-3 wt % salt, 0.5-3 wt % baking soda, 2-8 wt % flaxseed, 4-12 wt % oil, and a balance of water. One or more additional ingredients, including any of those described elsewhere herein may be added for additional flavoring, food product consistency, texture, etc. The water may be added to hydrate the dry *Aspergillus oryzae* and permit mixing or combing of the ingredients to form a dough or mixture. The dough is shaped and heated at a temperature of at least 150° C. for about 10 minutes to 40 minutes to reduce the water content and generate the animal treat food product.

Animal Treat Example 2

*Aspergillus oryzae* is dried prior to mixing into an animal treat food product to develop a umami flavor. The *Aspergillus oryzae* may be at least partially caramelized during drying. The food product is generated by combining 15-30 wt % dry *Aspergillus oryzae* with 10-15 wt % flour, 10-15 wt % potato starch, 0.5-3 wt % salt, 0.5-3 wt % baking soda, 2-8 wt % flaxseed, 10-30 wt % pumpkin puree, 4-12 wt % oil, 0.2-1 wt % natural flavors, and a balance of water. One or more additional ingredients, including any of those described elsewhere herein may be added for additional flavoring, food product consistency, texture, etc. The water may be added to hydrate the dry *Aspergillus oryzae* and permit mixing or combing of the ingredients to form a dough or mixture. The dough is shaped and heated at a temperature of at least 150° C. for about 10 minutes to 40 minutes to reduce the water content and generate the animal treat food product.

Animal Treat Example 3

An animal treat food product is generated by combining 30-50 wt % wet *Aspergillus oryzae* with 10-15 wt % flour, 20-30 wt % flaxseed, 10-15 wt % blueberries, and 4-12 wt % oil with a balance of water to form a dough or mixture. One or more additional ingredients, including any of those described elsewhere herein may be added for additional flavoring, food product consistency, texture, etc. The dough is shaped and heated at a temperature of at least 150° C. for about 10 minutes to 40 minutes to reduce the water content and generate the animal treat food product.

Animal Kibble Example 1

*Aspergillus oryzae* is dried prior to mixing into an animal kibble food product to develop a umami flavor. The *Aspergillus oryzae* may be at least partially caramelized during drying. The food product is be generated by combining 45-65 wt % dry *Aspergillus oryzae* with 18-25 wt % sunflower oil, 5-8 wt % dicalcium phosphate, 3-8 wt % flaxseed, 0.5-1.3 wt % mineral premix, 0.5-1.6 wt % salt, 0.5-1.6 wt % D,L-methionine, 0.5-1.6 wt % vitamin premix, 0.5-1.6 wt % potassium chloride, 0.2-0.8 wt % algal oil, and 0.2-0.8 wt % antioxidants and preservatives and a balance of water to form a dough or mixture. One or more additional ingredients, including any of those described elsewhere herein may be added for additional flavoring, food product consistency, texture, etc. The dough is shaped and heated at a temperature of at least 175° C. for about 5 minutes to 30 minutes to reduce the water content and generate the animal kibble food product.

Animal Kibble Example 2

*Aspergillus oryzae* is dried prior to mixing into an animal kibble food product to develop more umami flavor. The *Aspergillus oryzae* may be at least partially caramelized during drying. The food product is be generated by combining 3-10 wt % dry *Aspergillus oryzae* with 10-25 wt % yeast (e.g., *Saccharomyces cerevisiae*), 25-35 wt % flour, 0.5-1.6 wt % salt, 5-12 wt % flaxseed, 15-20 wt % sweet potato, 10-15 wt % oil, 0.8-1.5 wt % natural flavors, and 0.5-1.6 wt % vitamin and mineral premix and a balance of water to form a dough or mixture. One or more additional ingredients, including any of those described elsewhere herein may be added for additional flavoring, food product consistency, texture, etc. The dough is shaped and heated at a temperature of at least 175° C. to reduce the water content and generate the animal kibble food product.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A composition, comprising,
   (i) at least about 20% protein by dry weight, wherein said protein is not animal-derived protein,
   (ii) at least 20% by dry weight intact yeast cells,
   (iii) 20% to 70% plant-derived flour,
   (iv) at least 15% plant-derived starch selected from amylose, amylopectin and a combination thereof,
   (v) a vegetable oil, and
   (vi) a nutritional supplement comprising a plurality of vitamins and a plurality of minerals,
   wherein said composition has a water content that is less than or equal to about 30% water by weight,
   and wherein the product is produced by heat expanded extrusion.

2. The composition of claim 1, wherein said composition comprises at least about 30% fungal cells by dry weight.

3. The composition of claim 2, wherein said fungal cells further comprise one or more of *Aspergillus oryzae*, *Fusarium venenatum*, *Geotrichum candidum*, *Penicillium camemberti*, or *Penicillium roqueforti*.

4. The composition of claim 1, wherein said composition has a cutting force that is less than about 5 kilogram-force.

5. The composition of claim 1, wherein said composition has a density of from about 0.3 to 1.3 grams per cubic centimeter.

6. The composition of claim 1, wherein said water content is from about 15% to 30% by weight.

7. The composition of claim 1, wherein said water content is less than or equal to about 15% by weight.

8. The composition of claim 1, further comprising a non-animal heme-containing protein.

9. The composition of claim 1, further comprising at least about 4% by dry weight ribonucleic acids encoded by said one or more fungal genomes.

10. The composition of claim 9, further comprising at least about 6% by dry weight ribonucleic acids encoded by said one or more fungal genomes.

11. The composition of claim 1, further comprising bacteria.

12. The composition of claim 11, wherein said bacteria are selected from the group consisting of *Bifidobacterium bifidum, Lactobacillus acidophilus, Lactobacillus casei, Lactobacillus delbrueckii* subspecies *bulgaricus, Lactobacillus rhamnosus, Lactobacillus rhamnosus*, and combinations thereof.

13. The composition of claim 1, wherein said protein comprises an amino acid sequence encoded by one or more bacterial genomes.

14. The composition of claim 1, wherein said composition is a molded or shaped composition.

15. The composition of claim 1, wherein a portion of said protein is provided by one or more ingredients selected from pumpkin puree, squash puree, flax seed meal, flaxseed, nut butter, peanut butter, carrot powder, potato flour, sweet potato flour, potato powder, sweet potato powder, rice flour, oat flour, pea protein, ground peas, fruit dried potatoes, dried chickpeas, and chickpea flour.

16. The composition of claim 15, wherein said plant-derived flour comprises one or more of wheat flour, flaxseed flour, rice flour, corn flour, corn gluten, corn bran, corn starch, barley flour, sorghum flour, oat flour, potato flour, rye flour, soybean flour, buckwheat flour, or brown rice flour.

17. The composition of claim 16, comprising at least about 30% protein by dry weight.

18. The composition of claim 1, wherein said plant-derived flour is comprises one or more of wheat flour, flaxseed flour, rice flour, corn flour, corn gluten, corn bran, corn starch, barley flour, sorghum flour, oat flour, potato flour, rye flour, soybean flour, buckwheat flour, or brown rice flour.

19. The composition of claim 18, wherein the composition has a cutting force that is less than about 5 kilogram-force.

20. The composition of claim 1, comprising at least about 30% protein by dry weight.

21. The composition of claim 2, comprising at least about 30% protein by dry weight.

* * * * *